(12) United States Patent     (10) Patent No.:   US 12,622,784 B2

Nia et al.     (45) Date of Patent:     May 12, 2026

(54) HEART VALVE REPAIR

(71) Applicant: Edwards Lifesciences Corporation, Irvine, CA (US)

(72) Inventors: Nima V. Nia, Mission Viejo, CA (US); Hengchu Cao, Irvine, CA (US); Bingquan Su, Irvine, CA (US); Douglas Thomas Dominick, Irvine, CA (US); Sakyasingh Tripathy, San Diego, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1192 days.

(21) Appl. No.: 17/507,709

(22) Filed: Oct. 21, 2021

(65) Prior Publication Data

US 2022/0039954 A1    Feb. 10, 2022

Related U.S. Application Data

(63) Continuation of application No. PCT/US2020/027789, filed on Apr. 10, 2020.

(Continued)

(51) Int. Cl.
    *A61F 2/24*       (2006.01)

(52) U.S. Cl.
    CPC .......... *A61F 2/2463* (2013.01); *A61F 2/2454* (2013.01); *A61F 2/246* (2013.01); (Continued)

(58) Field of Classification Search
    CPC ...... A61F 2/2463; A61F 2/2454; A61F 2/246; A61F 2220/0016; A61F 2220/0075; (Continued)

(56) References Cited

U.S. PATENT DOCUMENTS

| | | | |
|---|---|---|---|
| 809,139 | A | 1/1906 | Saxton |
| 3,874,388 | A | 4/1975 | King et al. |

(Continued)

FOREIGN PATENT DOCUMENTS

| | | |
|---|---|---|
| CN | 1142351 A | 2/1997 |
| CN | 106175845 A | 12/2016 |

(Continued)

OTHER PUBLICATIONS

Al Zaibag et al., "Percutaneous Balloon Valvotomy in Tricuspid Stenosis", British Heart Journal, vol. 57, No. 1, Jan. 1987.

(Continued)

*Primary Examiner* — Sarah W Aleman
*Assistant Examiner* — Rachel S Highland
(74) *Attorney, Agent, or Firm* — Anya Adams

(57) ABSTRACT

A heart valve repair system includes an implantable device and a connector. The implantable device is configured to attach to at least two leaflets of a native heart valve of a patient and hold the at least two leaflets in a relatively fixed position. The connector is separate from the implantable device and includes first and second tissue anchors. The connector is configured to be attached to the at least two leaflets of the native valve when the at least two leaflets are held by the implantable device in the relatively fixed position. The implantable device is configured to be detached from the at least two leaflets and removed from the patient with the connector remaining attached to the at least two leaflets.

20 Claims, 22 Drawing Sheets

Related U.S. Application Data

(60) Provisional application No. 62/836,839, filed on Apr. 22, 2019.

(52) U.S. Cl.
CPC ................ *A61F 2220/0016* (2013.01); *A61F 2220/0075* (2013.01)

(58) Field of Classification Search
CPC ..... A61F 2220/0091; A61F 2250/0059; A61B 2017/00243; A61B 2017/00783; A61B 2017/0417; A61B 2017/0419; A61B 2017/0464; A61B 17/0401
See application file for complete search history.

(56) References Cited

U.S. PATENT DOCUMENTS

| | | | |
|---|---|---|---|
| 4,340,091 A | 7/1982 | Skelton et al. | |
| 4,506,669 A | 3/1985 | Blake | |
| 4,590,937 A | 5/1986 | Deniega | |
| 4,693,248 A | 9/1987 | Failla | |
| 4,803,983 A | 2/1989 | Siegel | |
| 5,125,895 A | 6/1992 | Buchbinder et al. | |
| 5,171,252 A | 12/1992 | Friedland | |
| 5,195,962 A | 3/1993 | Martin et al. | |
| 5,292,326 A | 3/1994 | Green et al. | |
| 5,327,905 A | 7/1994 | Avitall | |
| 5,363,861 A | 11/1994 | Edwards et al. | |
| 5,370,685 A | 12/1994 | Stevens | |
| 5,389,077 A | 2/1995 | Melinyshyn et al. | |
| 5,411,552 A | 5/1995 | Andersen et al. | |
| 5,450,860 A | 9/1995 | O'Connor | |
| 5,456,674 A | 10/1995 | Bos et al. | |
| 5,474,057 A | 12/1995 | Makower et al. | |
| 5,478,353 A | 12/1995 | Yoon | |
| 5,487,746 A | 1/1996 | Yu et al. | |
| 5,565,004 A | 10/1996 | Christoudias | |
| 5,607,462 A | 3/1997 | Imran | |
| 5,609,598 A | 3/1997 | Laufer et al. | |
| 5,611,794 A | 3/1997 | Sauer et al. | |
| 5,626,607 A | 5/1997 | Malecki et al. | |
| 5,683,418 A * | 11/1997 | Luscombe | A61B 17/0401 |
| | | | 606/907 |
| 5,695,504 A | 12/1997 | Gifford et al. | |
| 5,716,417 A | 2/1998 | Girard et al. | |
| 5,727,569 A | 3/1998 | Benetti et al. | |
| 5,741,297 A | 4/1998 | Simon | |
| 5,782,746 A | 7/1998 | Wright | |
| 5,797,960 A | 8/1998 | Stevens et al. | |
| 5,836,311 A | 11/1998 | Borst et al. | |
| 5,843,076 A | 12/1998 | Webster et al. | |
| 5,855,590 A | 1/1999 | Malecki et al. | |
| 5,885,271 A | 3/1999 | Hamilton et al. | |
| 5,888,247 A | 3/1999 | Benetti | |
| 5,891,017 A | 4/1999 | Swindle et al. | |
| 5,891,112 A | 4/1999 | Samson | |
| 5,894,843 A | 4/1999 | Benetti et al. | |
| 5,921,979 A | 7/1999 | Kovac et al. | |
| 5,944,738 A | 8/1999 | Amplatz et al. | |
| 5,957,835 A | 9/1999 | Anderson et al. | |
| 5,972,020 A | 10/1999 | Carpentier et al. | |
| 5,980,534 A | 11/1999 | Gimpelson | |
| 6,004,329 A | 12/1999 | Myers et al. | |
| 6,010,531 A | 1/2000 | Donlon et al. | |
| 6,017,358 A | 1/2000 | Yoon et al. | |
| 6,086,600 A | 7/2000 | Kortenbach | |
| 6,120,496 A | 9/2000 | Whayne et al. | |
| 6,132,370 A | 10/2000 | Furnish et al. | |
| 6,162,239 A | 12/2000 | Manhes | |
| 6,165,183 A | 12/2000 | Kuehn et al. | |
| 6,182,664 B1 | 2/2001 | Cosgrove | |
| 6,193,732 B1 | 2/2001 | Frantzen et al. | |
| 6,193,734 B1 | 2/2001 | Bolduc et al. | |
| 6,200,315 B1 | 3/2001 | Gaiser et al. | |
| 6,228,032 B1 | 5/2001 | Eaton et al. | |
| 6,241,743 B1 | 6/2001 | Levin et al. | |
| 6,269,819 B1 | 8/2001 | Oz et al. | |
| 6,269,829 B1 | 8/2001 | Chen et al. | |
| 6,312,447 B1 | 11/2001 | Grimes | |
| 6,461,366 B1 | 10/2002 | Seguin | |
| 6,468,285 B1 | 10/2002 | Hsu et al. | |
| 6,508,806 B1 | 1/2003 | Hoste | |
| 6,508,825 B1 | 1/2003 | Selmon et al. | |
| 6,530,933 B1 | 3/2003 | Yeung et al. | |
| 6,537,290 B2 | 3/2003 | Adams et al. | |
| 6,544,215 B1 | 4/2003 | Bencini et al. | |
| 6,626,930 B1 | 9/2003 | Allen et al. | |
| 6,629,534 B1 | 10/2003 | St Goar et al. | |
| 6,719,767 B1 | 4/2004 | Kimblad | |
| 6,764,510 B2 | 7/2004 | Vidlund et al. | |
| 6,770,083 B2 | 8/2004 | Seguin | |
| 6,837,867 B2 | 1/2005 | Kortelling | |
| 6,855,137 B2 | 2/2005 | Bon | |
| 6,913,614 B2 | 7/2005 | Marino et al. | |
| 6,939,337 B2 | 9/2005 | Parker et al. | |
| 6,945,956 B2 | 9/2005 | Waldhauser et al. | |
| 7,048,754 B2 | 5/2006 | Martin et al. | |
| 7,101,395 B2 | 9/2006 | Tremulis et al. | |
| 7,125,421 B2 | 10/2006 | Tremulis et al. | |
| 7,288,097 B2 | 10/2007 | Séguin | |
| 7,371,210 B2 | 5/2008 | Brock et al. | |
| 7,464,712 B2 | 12/2008 | Oz et al. | |
| 7,509,959 B2 | 3/2009 | Oz et al. | |
| 7,569,062 B1 | 8/2009 | Kuehn et al. | |
| 7,618,449 B2 | 11/2009 | Tremulis et al. | |
| 7,682,369 B2 | 3/2010 | Séguin | |
| 7,731,706 B2 | 6/2010 | Potter | |
| 7,744,609 B2 | 6/2010 | Allen et al. | |
| 7,748,389 B2 | 7/2010 | Salahieh et al. | |
| 7,753,932 B2 | 7/2010 | Gingrich et al. | |
| 7,758,596 B2 | 7/2010 | Oz et al. | |
| 7,780,723 B2 | 8/2010 | Taylor | |
| 7,803,185 B2 | 9/2010 | Gabbay | |
| 7,824,443 B2 | 11/2010 | Salahieh et al. | |
| 7,981,123 B2 | 7/2011 | Séguin | |
| 7,988,724 B2 | 8/2011 | Salahieh et al. | |
| 8,052,750 B2 | 11/2011 | Tuval et al. | |
| 8,070,805 B2 | 12/2011 | Vidlund et al. | |
| 8,096,985 B2 | 1/2012 | Legaspi et al. | |
| 8,104,149 B1 | 1/2012 | McGarity | |
| 8,133,239 B2 | 3/2012 | Oz et al. | |
| 8,147,542 B2 | 4/2012 | Maisano et al. | |
| 8,172,856 B2 | 5/2012 | Eigler et al. | |
| 8,206,437 B2 | 6/2012 | Bonhoeffer et al. | |
| 8,216,301 B2 | 7/2012 | Bonhoeffer et al. | |
| 8,303,653 B2 | 11/2012 | Bonhoeffer et al. | |
| 8,313,525 B2 | 11/2012 | Tuval et al. | |
| 8,348,995 B2 | 1/2013 | Tuval et al. | |
| 8,348,996 B2 | 1/2013 | Tuval et al. | |
| 8,414,643 B2 | 4/2013 | Tuval et al. | |
| 8,425,404 B2 | 4/2013 | Wilson et al. | |
| 8,449,599 B2 | 5/2013 | Chau et al. | |
| 8,449,606 B2 | 5/2013 | Eliasen et al. | |
| 8,460,368 B2 | 6/2013 | Taylor et al. | |
| 8,470,028 B2 | 6/2013 | Thornton et al. | |
| 8,480,730 B2 | 7/2013 | Maurer et al. | |
| 8,540,767 B2 | 9/2013 | Zhang | |
| 8,579,965 B2 | 11/2013 | Bonhoeffer et al. | |
| 8,585,756 B2 | 11/2013 | Bonhoeffer et al. | |
| 8,652,202 B2 | 2/2014 | Alon et al. | |
| 8,668,733 B2 | 3/2014 | Haug et al. | |
| 8,721,665 B2 | 5/2014 | Oz et al. | |
| 8,740,918 B2 | 6/2014 | Seguin | |
| 8,771,347 B2 | 7/2014 | DeBoer et al. | |
| 8,778,017 B2 | 7/2014 | Eliasen et al. | |
| 8,834,564 B2 | 9/2014 | Tuval et al. | |
| 8,840,663 B2 | 9/2014 | Salahieh et al. | |
| 8,876,894 B2 | 11/2014 | Tuval et al. | |
| 8,876,895 B2 | 11/2014 | Tuval et al. | |
| 8,945,177 B2 | 2/2015 | Dell et al. | |
| 9,034,032 B2 | 5/2015 | McLean et al. | |
| 9,198,757 B2 | 12/2015 | Schroeder et al. | |
| 9,220,507 B1 | 12/2015 | Patel et al. | |

(56) References Cited

U.S. PATENT DOCUMENTS

| | | | |
|---|---|---|---|
| 9,259,317 | B2 | 2/2016 | Wilson et al. |
| 9,282,972 | B1 | 3/2016 | Patel et al. |
| 9,301,834 | B2 | 4/2016 | Tuval et al. |
| 9,308,360 | B2 | 4/2016 | Bishop et al. |
| 9,387,071 | B2 | 7/2016 | Tuval et al. |
| 9,427,327 | B2 | 8/2016 | Parrish |
| 9,439,763 | B2 | 9/2016 | Geist et al. |
| 9,510,837 | B2 | 12/2016 | Seguin |
| 9,510,946 | B2 | 12/2016 | Chau et al. |
| 9,572,660 | B2 | 2/2017 | Braido et al. |
| 9,642,704 | B2 | 5/2017 | Tuval et al. |
| 9,700,445 | B2 | 7/2017 | Martin et al. |
| 9,775,963 | B2 | 10/2017 | Miller |
| 9,889,002 | B2 | 2/2018 | Bonhoeffer et al. |
| 9,949,824 | B2 | 4/2018 | Bonhoeffer et al. |
| 10,076,327 | B2 | 9/2018 | Ellis et al. |
| 10,076,415 | B1 | 9/2018 | Metchik et al. |
| 10,099,050 | B2 | 10/2018 | Chen et al. |
| 10,105,221 | B2 | 10/2018 | Siegel |
| 10,105,222 | B1 | 10/2018 | Metchik et al. |
| 10,111,751 | B1 | 10/2018 | Metchik et al. |
| 10,123,873 | B1 | 11/2018 | Metchik et al. |
| 10,130,475 | B1 | 11/2018 | Metchik et al. |
| 10,136,993 | B1 | 11/2018 | Metchik et al. |
| 10,159,570 | B1 | 12/2018 | Metchik et al. |
| 10,226,309 | B2 | 3/2019 | Ho et al. |
| 10,231,837 | B1 | 3/2019 | Metchik et al. |
| 10,238,493 | B1 | 3/2019 | Metchik et al. |
| 10,238,494 | B2 | 3/2019 | McNiven et al. |
| 10,238,495 | B2 | 3/2019 | Marsot et al. |
| 10,299,924 | B2 | 5/2019 | Kizuka |
| 10,376,673 | B2 | 8/2019 | Van Hoven et al. |
| 10,575,841 | B1 | 3/2020 | Paulos |
| 2001/0005787 | A1 | 6/2001 | Oz et al. |
| 2002/0013571 | A1 | 1/2002 | Goldfarb et al. |
| 2002/0107531 | A1 | 8/2002 | Schreck et al. |
| 2002/0173811 | A1 | 11/2002 | Tu et al. |
| 2002/0183787 | A1 | 12/2002 | Wahr et al. |
| 2003/0130731 | A1* | 7/2003 | Vidlund ................ A61F 2/2454 |
| | | | 623/2.37 |
| 2003/0144573 | A1 | 7/2003 | Heilman et al. |
| 2003/0187467 | A1 | 10/2003 | Schreck |
| 2003/0208231 | A1 | 11/2003 | Williamson et al. |
| 2004/0003819 | A1 | 1/2004 | St. Goar et al. |
| 2004/0030382 | A1 | 2/2004 | St. Goar et al. |
| 2004/0034365 | A1 | 2/2004 | Lentz et al. |
| 2004/0044350 | A1 | 3/2004 | Martin et al. |
| 2004/0044365 | A1 | 3/2004 | Bachman |
| 2004/0049207 | A1 | 3/2004 | Goldfarb et al. |
| 2004/0122448 | A1 | 6/2004 | Levine |
| 2004/0127981 | A1 | 7/2004 | Rahdert et al. |
| 2004/0127982 | A1 | 7/2004 | Machold et al. |
| 2004/0147943 | A1 | 7/2004 | Kobayashi |
| 2004/0181135 | A1 | 9/2004 | Drysen |
| 2004/0181206 | A1 | 9/2004 | Chiu et al. |
| 2004/0181238 | A1 | 9/2004 | Zarbatany et al. |
| 2004/0210307 | A1 | 10/2004 | Khairkhahan |
| 2004/0220593 | A1 | 11/2004 | Greenhalgh |
| 2005/0010287 | A1 | 1/2005 | Macoviak et al. |
| 2005/0049618 | A1 | 3/2005 | Masuda et al. |
| 2005/0070926 | A1 | 3/2005 | Ortiz |
| 2005/0137690 | A1 | 6/2005 | Salahieh et al. |
| 2005/0143767 | A1 | 6/2005 | Kimura et al. |
| 2005/0165429 | A1 | 7/2005 | Douglas et al. |
| 2005/0216039 | A1 | 9/2005 | Lederman |
| 2005/0251177 | A1 | 11/2005 | Saadat et al. |
| 2005/0251183 | A1 | 11/2005 | Buckman et al. |
| 2005/0288786 | A1 | 12/2005 | Chanduszko |
| 2006/0020275 | A1 | 1/2006 | Goldfarb et al. |
| 2006/0089671 | A1 | 4/2006 | Goldfarb et al. |
| 2006/0100649 | A1 | 5/2006 | Hart |
| 2006/0122647 | A1 | 6/2006 | Callaghan et al. |
| 2006/0142694 | A1 | 6/2006 | Bednarek et al. |
| 2006/0173251 | A1 | 8/2006 | Govari et al. |
| 2006/0178700 | A1 | 8/2006 | Quinn |

| | | | |
|---|---|---|---|
| 2006/0224169 | A1 | 10/2006 | Weisenburgh et al. |
| 2007/0010800 | A1 | 1/2007 | Weitzner et al. |
| 2007/0010877 | A1 | 1/2007 | Salahieh et al. |
| 2007/0016286 | A1 | 1/2007 | Herrmann et al. |
| 2007/0021779 | A1 | 1/2007 | Garvin et al. |
| 2007/0032807 | A1 | 2/2007 | Ortiz et al. |
| 2007/0093857 | A1 | 4/2007 | Rogers et al. |
| 2007/0093890 | A1 | 4/2007 | Eliasen et al. |
| 2007/0156197 | A1 | 7/2007 | Root et al. |
| 2007/0191154 | A1 | 8/2007 | Genereux et al. |
| 2007/0197858 | A1 | 8/2007 | Goldfarb et al. |
| 2007/0198038 | A1 | 8/2007 | Cohen et al. |
| 2007/0265700 | A1 | 11/2007 | Eliasen et al. |
| 2007/0282414 | A1 | 12/2007 | Soltis et al. |
| 2007/0293943 | A1 | 12/2007 | Quinn |
| 2007/0299387 | A1 | 12/2007 | Williams et al. |
| 2007/0299424 | A1 | 12/2007 | Cumming et al. |
| 2008/0039743 | A1 | 2/2008 | Fox et al. |
| 2008/0039953 | A1 | 2/2008 | Davis et al. |
| 2008/0065149 | A1 | 3/2008 | Thielen et al. |
| 2008/0077144 | A1 | 3/2008 | Crofford |
| 2008/0091169 | A1 | 4/2008 | Heideman et al. |
| 2008/0125861 | A1* | 5/2008 | Webler ................ A61B 17/064 |
| | | | 623/2.36 |
| 2008/0140089 | A1 | 6/2008 | Kogiso et al. |
| 2008/0147093 | A1 | 6/2008 | Roskopf et al. |
| 2008/0147112 | A1 | 6/2008 | Sheets et al. |
| 2008/0149685 | A1 | 6/2008 | Smith et al. |
| 2008/0167713 | A1 | 7/2008 | Bolling |
| 2008/0177300 | A1 | 7/2008 | Mas et al. |
| 2008/0208332 | A1 | 8/2008 | Lamphere et al. |
| 2008/0221672 | A1 | 9/2008 | Lamphere et al. |
| 2008/0255427 | A1 | 10/2008 | Satake et al. |
| 2008/0281411 | A1 | 11/2008 | Berreklouw |
| 2008/0287862 | A1 | 11/2008 | Weitzner et al. |
| 2008/0294247 | A1 | 11/2008 | Yang et al. |
| 2008/0312506 | A1 | 12/2008 | Spivey et al. |
| 2008/0319455 | A1 | 12/2008 | Harris et al. |
| 2009/0005863 | A1 | 1/2009 | Goetz et al. |
| 2009/0024110 | A1 | 1/2009 | Heideman et al. |
| 2009/0131880 | A1 | 5/2009 | Speziali et al. |
| 2009/0156995 | A1 | 6/2009 | Martin et al. |
| 2009/0163934 | A1 | 6/2009 | Raschdorf et al. |
| 2009/0166913 | A1 | 7/2009 | Guo et al. |
| 2009/0177266 | A1 | 7/2009 | Powell et al. |
| 2009/0234280 | A1 | 9/2009 | Tah et al. |
| 2009/0275902 | A1 | 11/2009 | Heeps et al. |
| 2009/0287304 | A1 | 11/2009 | Dahlgren et al. |
| 2010/0022823 | A1 | 1/2010 | Goldfarb et al. |
| 2010/0057192 | A1 | 3/2010 | Celermajer |
| 2010/0069834 | A1 | 3/2010 | Schultz |
| 2010/0094317 | A1 | 4/2010 | Goldfarb et al. |
| 2010/0106141 | A1 | 4/2010 | Osypka et al. |
| 2010/0121434 | A1 | 5/2010 | Paul et al. |
| 2010/0249497 | A1 | 9/2010 | Peine et al. |
| 2010/0298929 | A1 | 11/2010 | Thornton et al. |
| 2010/0324595 | A1 | 12/2010 | Linder et al. |
| 2011/0082538 | A1 | 4/2011 | Dahlgren et al. |
| 2011/0137410 | A1 | 6/2011 | Hacohen |
| 2011/0245855 | A1 | 10/2011 | Matsuoka et al. |
| 2011/0257723 | A1 | 10/2011 | McNamara |
| 2011/0295281 | A1 | 12/2011 | Mizumoto et al. |
| 2012/0022633 | A1 | 1/2012 | Olson et al. |
| 2012/0089125 | A1 | 4/2012 | Scheibe et al. |
| 2012/0109160 | A1 | 5/2012 | Martinez et al. |
| 2012/0116419 | A1 | 5/2012 | Sigmon |
| 2012/0209318 | A1 | 8/2012 | Qadeer |
| 2012/0277853 | A1 | 11/2012 | Rothstein |
| 2013/0035759 | A1 | 2/2013 | Gross et al. |
| 2013/0041314 | A1 | 2/2013 | Dillon |
| 2013/0066341 | A1 | 3/2013 | Ketai et al. |
| 2013/0066342 | A1 | 3/2013 | Dell et al. |
| 2013/0072945 | A1 | 3/2013 | Terada |
| 2013/0073034 | A1 | 3/2013 | Wilson et al. |
| 2013/0110254 | A1 | 5/2013 | Osborne |
| 2013/0190798 | A1 | 7/2013 | Kapadia |
| 2013/0190861 | A1 | 7/2013 | Chau et al. |
| 2013/0268069 | A1 | 10/2013 | Zakai et al. |
| 2013/0282059 | A1 | 10/2013 | Ketai et al. |

(56) References Cited

U.S. PATENT DOCUMENTS

| | | |
|---|---|---|
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0222136 A1 | 8/2014 | Geist et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277404 A1 | 9/2014 | Wilson et al. |
| 2014/0277411 A1 | 9/2014 | Börtlein et al. |
| 2014/0277427 A1 | 9/2014 | Ratz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0148896 A1 | 5/2015 | Karapetian et al. |
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008129 A1 | 1/2016 | Siegel |
| 2016/0008131 A1 | 1/2016 | Christianson et al. |
| 2016/0022970 A1 | 1/2016 | Forcucci et al. |
| 2016/0051796 A1 | 2/2016 | Kanemasa et al. |
| 2016/0074164 A1 | 3/2016 | Naor |
| 2016/0074165 A1 | 3/2016 | Spence et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0302811 A1 | 10/2016 | Rodriguez-Navarro et al. |
| 2016/0317290 A1 | 11/2016 | Chau et al. |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100119 A1 | 4/2017 | Baird et al. |
| 2017/0100236 A1 | 4/2017 | Robertson et al. |
| 2017/0224955 A1 | 8/2017 | Douglas et al. |
| 2017/0239048 A1 | 8/2017 | Goldfarb et al. |
| 2017/0252154 A1 | 9/2017 | Tubishevitz et al. |
| 2017/0266413 A1 | 9/2017 | Khuu et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0071487 A1 | 3/2018 | Khuu et al. |
| 2018/0078271 A1 | 3/2018 | Thrasher |
| 2018/0078361 A1 | 3/2018 | Naor et al. |
| 2018/0092661 A1 | 4/2018 | Prabhu |
| 2018/0126124 A1 | 5/2018 | Winston et al. |
| 2018/0133008 A1 | 5/2018 | Kizuka et al. |
| 2018/0146964 A1 | 5/2018 | Garcia et al. |
| 2018/0146966 A1 | 5/2018 | Hernández et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0185154 A1 | 7/2018 | Cao |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0117113 A1 | 4/2019 | Curran |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0183644 A1 | 6/2019 | Hacohen |
| 2019/0192296 A1 | 6/2019 | Schwartz et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2019/0321166 A1 | 10/2019 | Freschauf et al. |
| 2020/0113683 A1 | 4/2020 | Dale et al. |
| 2020/0138569 A1 | 5/2020 | Basude et al. |
| 2020/0205979 A1 | 7/2020 | O'Carroll et al. |
| 2020/0237512 A1 | 7/2020 | McCann et al. |
| 2020/0337842 A1 | 10/2020 | Metchik et al. |

(56) References Cited

U.S. PATENT DOCUMENTS

| | | |
|---|---|---|
| 2020/0352717 A1 | 11/2020 | Kheradvar et al. |
| 2020/0360054 A1 | 11/2020 | Walsh et al. |
| 2020/0360132 A1 | 11/2020 | Spence |
| 2020/0368016 A1 | 11/2020 | Pesce et al. |
| 2021/0022850 A1 | 1/2021 | Basude et al. |
| 2021/0059680 A1 | 3/2021 | Lin et al. |
| 2021/0169650 A1 | 6/2021 | Dai et al. |
| 2021/0186698 A1 | 6/2021 | Abunassar et al. |
| 2021/0251757 A1 | 8/2021 | Siegel et al. |
| 2021/0259835 A1 | 8/2021 | Tyler et al. |
| 2021/0267781 A1 | 9/2021 | Metchik et al. |
| 2021/0307900 A1 | 10/2021 | Hacohen |
| 2021/0330456 A1 | 10/2021 | Hacohen et al. |
| 2021/0338418 A1 | 11/2021 | Feld |
| 2021/0361238 A1 | 11/2021 | Bak-Boychuk et al. |
| 2021/0361416 A1 | 11/2021 | Stearns |
| 2021/0361422 A1 | 11/2021 | Gross et al. |
| 2021/0361428 A1 | 11/2021 | Dixon |
| 2021/0378818 A1 | 12/2021 | Manash et al. |
| 2021/0401434 A1 | 12/2021 | Tien et al. |
| 2022/0039943 A1 | 2/2022 | Phan |
| 2022/0039954 A1 | 2/2022 | Nia et al. |
| 2022/0071767 A1 | 3/2022 | Dixon et al. |
| 2022/0133327 A1 | 5/2022 | Zhang et al. |
| 2022/0142780 A1 | 5/2022 | Zhang et al. |
| 2022/0142781 A1 | 5/2022 | Zhang et al. |
| 2022/0226108 A1 | 7/2022 | Freschauf et al. |
| 2022/0233312 A1 | 7/2022 | Delgado et al. |
| 2022/0257196 A1 | 8/2022 | Massmann |
| 2022/0287841 A1 | 9/2022 | Freschauf et al. |
| 2022/0296248 A1 | 9/2022 | Abunassar et al. |
| 2022/0313433 A1 | 10/2022 | Ma et al. |
| 2023/0014540 A1 | 1/2023 | Metchik et al. |
| 2023/0149170 A1 | 5/2023 | Giese et al. |
| 2023/0218291 A1 | 7/2023 | Zarbatany et al. |
| 2023/0270549 A1 | 8/2023 | Guidotti et al. |
| 2024/0148505 A1 | 5/2024 | Datta et al. |

FOREIGN PATENT DOCUMENTS

| | | |
|---|---|---|
| CN | 106491245 A | 3/2017 |
| CN | 107789017 A | 3/2018 |
| CN | 109953779 A | 7/2019 |
| CN | 110338857 A | 10/2019 |
| CN | 110495972 A | 11/2019 |
| CN | 110537946 A | 12/2019 |
| CN | 110664515 A | 1/2020 |
| CN | 209996540 U | 1/2020 |
| CN | 211243911 U | 8/2020 |
| CN | 211723546 U | 10/2020 |
| CN | 111870398 A | 11/2020 |
| CN | 111904660 A | 11/2020 |
| CN | 112120831 A | 12/2020 |
| CN | 112168427 A | 1/2021 |
| CN | 112190367 A | 1/2021 |
| CN | 212346813 U | 1/2021 |
| CN | 212415988 U | 1/2021 |
| CN | 212490263 U | 2/2021 |
| CN | 113476182 A | 10/2021 |
| CN | 113855328 A | 12/2021 |
| CN | 215019733 U | 12/2021 |
| EP | 0098100 A2 | 1/1984 |
| FR | 2768324 B1 | 3/1999 |
| WO | 2014064694 A2 | 5/2014 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |
| WO | 2020106705 A1 | 5/2020 |
| WO | 2020106827 A1 | 5/2020 |
| WO | 2020112622 A1 | 6/2020 |
| WO | 2020167677 A1 | 8/2020 |
| WO | 2020168081 A1 | 8/2020 |
| WO | 2020172224 A1 | 8/2020 |
| WO | 2020176410 A1 | 9/2020 |
| WO | 2021196580 A1 | 10/2021 |
| WO | 2021227412 A1 | 11/2021 |
| WO | 2022006087 A2 | 1/2022 |
| WO | 2022036209 A1 | 2/2022 |
| WO | 2022051241 A1 | 3/2022 |
| WO | 2022052506 A1 | 3/2022 |
| WO | 2022068188 A1 | 4/2022 |
| WO | 2022101817 A2 | 5/2022 |
| WO | 2022140175 A1 | 6/2022 |
| WO | 2022153131 A1 | 7/2022 |
| WO | 2022155298 A2 | 7/2022 |
| WO | 2022157592 A1 | 7/2022 |
| WO | 2022212172 A1 | 10/2022 |
| WO | 2023003755 A1 | 1/2023 |
| WO | 2023004098 A1 | 1/2023 |
| WO | 2023278663 A2 | 1/2023 |
| WO | 2023288003 A1 | 1/2023 |

OTHER PUBLICATIONS

Al-Khaja et al., "Eleven years' experience with Carpentier-Edwards biological valves in relation to survival and complications", European Journal of Cardio-Thoracic Surgery, vol. 3, No. 4, pp. 305-311, Jul. 1, 1989, Springer-Verlag, Berlin, Germany.

Almagor et al., "Balloon Expandable Stent Implantation in Stenotic Right Heart Valved Conduits", Journal of the American College of Cardiology, vol. 16, No. 5, pp. 1310-1314, Nov. 15, 1990.

Andersen, et al., "Transluminal implantation of artificial heart valves. Description of a new expandable aortic valve and initial results with implantation by catheter technique in closed chest pigs", European Heart Journal, vol. 13, No. 5, pp. 704-708, May 1, 1992, The European Society of Cardiology, Oxford University Press, United Kingdom.

Andersen, H.R. "History of Percutaneous Aortic Valve Prosthesis," Herz, vol. 34., No. 5, pp. 343-346, Aug. 2009, Urban&Vogel, Germany.

Batista RJ et al., "Partial left ventriculectomy to treat end-stage heart disease", Ann Thorac Surg., vol. 64, Issue-3, pp. 634-638, Sep. 1997.

Beall AC Jr. et al., "Clinical experience with a dacron velour-covered teflon-disc mitral-valve prosthesis", Ann Thorac Surg., vol. 5, Issue 5, pp. 402-410, May 1968.

Benchimol et al., "Simultaneous left ventricular echocardiography and aortic blood velocity during rapid right ventricular pacing in man", The American Journal of the Medical Sciences, vol. 273, No. 1, pp. 55-62, Jan.-Feb. 1977, Elsevier, United States.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, No. 30, pp. 654-670, Nov. 1, 1964, Lippincott Williams&Wilkins, Philadelphia, PA.

Fucci et al., "Improved results with mitral valve repair using new surgical techniques", Eur J Cardiothorac Surg. 1995;Issue 9, vol. 11, pp. 621-626.

Inoune et al., "Clinical application of transvenous mitral commissurotomy by a new balloon catheter," The Journal of Thoracic and Cardiovascular Surgery, vol. 87, No. 3, pp. 394-402, Mar. 1984, Elsevier, United States.

Kolata, Gina "Device That Opens Clogged Arteries Gets a Failing Grade in a New Study", The New York Times, Jan. 3, 1991, pp. 1-2 [online], [retrieved on Jul. 29, 2009]. Retrieved from the Internet <URL:http://www.nytimes.com/1991/01/03/health/device-that-opens-clogged-arteries-gets-a-faili . . . .

Lawrence, Jr., et al., "Percutaneous Endovascular Graft: Experimental Evaluation", Cardiovascular Radiology 163, pp. 357-360, May 1987.

(56) References Cited

OTHER PUBLICATIONS

Maisano F et al., 'The edge-to-edge technique: a simplified method to correct mitral insufficiency', Eur J Cardiothorac Surg., vol. 13, Issue-3, pp. 240-5, Mar. 1998.

Pavcnik et al., "Development and Initial Experimental Evaluation of a Prosthetic Aortic Valve for Transcatheter Placement," Radiology, vol. 183, No. 1, pp. 151-154, Apr. 1, 1992. Elsevier, United States.

Reul RM et al., "Mitral valve reconstruction for mitral insufficiency", Prog Cardiovasc Dis., vol. 39, Issue-6, May-Jun. 1997.

Rösch et al., "The Birth, Early Years and Future of Interventional Radiology," Journal of Vascular and Interventional Radiology, vol. 14, No. 7, pp. 841-853, Jul. 1, 2003, Elsevier, United States.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology, vol. 176, No. 2, pp. 535-538, Jul. 31, 1990, Radiological Society of North America, Oak Brook, IL.

Serruys et al., "Stenting of coronary arteries. Are we the sorcerer's apprentice?", European Heart Journal, vol. 10, No. 9 pp. 774-782, Sep. 1, 1989, The European Society of Cardiology, Oxford University Press, United Kingdom.

Sigwart, Ulrich, "An Overview of Intravascular Stents: Old and New," Textbook of Interventional Cardiology, Second Edition, chapter 48, pp. 803-815, © 1994, W.B. Saunders Company, Philadelphia, PA.

Uchida et al., "Modifications of Gianturco Expandable Wire Stents", Technical Note, American Roentgen Ray Society, pp. 1185-1187, May 1988.

Umaña Jp et al., Bow-tie' mitral valve repair: an adjuvant technique for ischemic mitral regurgitation', Ann Thorac Surg., vol. 66, Issue-6, pp. 1640-1646, Nov. 1998.

Urban, Philip MD, "Coronary Artery Stenting", pp. 5-47, © 1991, ISBN: 2-88049-054-5, Editions Medecine et Hygiene, Geneva, Switzerland.

Watt et al., "Intravenous adenosine in the treatment of supraventricular rachycardia: a dose-ranging study and interaction with dipyridamole", British Journal of Clinical Pharmacology, vol. 21, No. 2, pp. 227-230, Feb. 1986, British Pharmacological Society, London, United Kingdom.

Wheatley, David J., "Valve Prosthesis", Rob&Smith's Operative Surgery—Cardiac Surgery, vol. 91, No. 2, pp. 415-424, Feb. 1, 1987, Butterworth Scientific, London, UK.

Praz et al., "Compassionate use of the Pascal transcatheter mitral valve repair system for patients with severe mitral regurgitation: a multicentre, prospective, observational, first-in-man study," The Lancet, vol. 390, Issue 10096, pp. 773-780, Aug. 19, 2017, Lancet, United States.

Grasso et al., "The Pascal transcatheter mitral valve repair system for the treatment of mitral regurgitation: another piece to the puzzle of edge-to-edge technique", Journal of Thoracic Disease, vol. 9, No. 12, pp. 4856-4859, Dec. 2017, doi: 10.21037/jtd.2017.10.156, AME Publishing Company, Hong Kong, China.

Ross, D.N, "Aortic Valve Surgery", Surgery of the Aortic Valves, Guy's Hospital, London, pp. 192-197 [Removed Per Bim On Oct. 9, 2020].

Rashkind et al., "Historical Aspects of Interventional Cardiology: Past, Present, and Future", vol. 13, No. 4, pp. 363-367, Dec. 1986, Texas Heart Institute Journal, Interventional Cardiology, Houston, TX. [Dec. 22, 2020].

Rashkind et al., "Creation of an Atrial Septal Defect Without Thoracotomy: A Pallative Approach to Complete Transposition of the Great Arteries", The Journal of the American Medical Association, vol. 196, No. 11, pp. 173-174, Jun. 13, 1966 [Dec. 22, 2020].

* cited by examiner

HEART VALVE REPAIR

RELATED APPLICATION

This application is a continuation of PCT application no. PCT/US2020/027789, filed on Apr. 10, 2020, which claims priority to U.S. Provisional Application No. 62/836,839, filed on Apr. 22, 2019, entitled HEART VALVE REPAIR SYSTEM, the disclosure of which is hereby incorporated by reference in its entirety.

BACKGROUND

Field

The present disclosure generally relates to the field of medical devices and procedures.

Description of Related Art

The native heart valves (i.e., the aortic, pulmonary, tricuspid, and mitral valves) of the human heart aid in the circulation blood through the cardiovascular system. These heart valves can be damaged, and thus rendered less effective, by congenital malformations, inflammatory processes, infectious conditions, or disease.

SUMMARY

The disclosure describes, in one aspect, an implantable valve repair system for repairing a native valve of a patient. The implantable valve repair system for repairing a native valve of a patient includes an implantable prosthetic device and a connector. The implantable prosthetic device is configured to attach to two leaflets of the native valve of the patient. The connector is separate from the implantable prosthetic device and is also configured to attach to the two leaflets of the native valve of the patient. The implantable prosthetic device is configured both to allow the implantable prosthetic device to remain attached to the native valve after the connector is attached to the native valve and to allow the implantable prosthetic device to be removed from the native valve after the connector is attached to the native valve.

In some implementations, the present disclosure relates to a heart valve repair system comprising an implantable prosthetic device configured to attach to at least two leaflets of a native heart valve of a patient and hold the at least two leaflets in a relatively fixed position, and a connector that is separate from the implantable prosthetic device, the connector including first and second tissue anchors and being configured to be attached to the at least two leaflets of the native valve of the patient when the at least two leaflets are held by the implantable prosthetic device in the relatively fixed position, the implantable prosthetic device being configured to be detached from the at least two leaflets and removed from the patient with the connector remaining attached to the at least two leaflets.

The implantable prosthetic device may include a plurality of paddles that each comprise an inner paddle portion and an outer paddle portion. In some embodiments, the implantable prosthetic device includes a coaption element. For example, the paddles can be connected to a distal end of the coaption element. The prosthetic device and the connector can be configured to close a gap in the native valve of the patient when the valve repair system is attached to the native valve.

The connector can be configured to keep the gap in the native valve of the patient closed after the prosthetic device is removed.

The heart valve repair system can further comprise one or more additional connectors. The connector can comprise a first anchor configured to be positioned on a ventricular side of a first leaflet of the at least two leaflets, a second anchor configured to be positioned on a ventricular side of a second leaflet of the at least two leaflets, and a connecting portion including one or more suture lines coupled to the first and second anchors and configured to extend through the first leaflet and the second leaflet.

In some embodiments, the connecting portion comprises a first suture line extending from the first anchor through the first leaflet, a second suture line extending from the second anchor through the second leaflet, and a suture-locking device engaging both the first suture line and the second suture line to hold the first leaflet and the second leaflet together. For example, the suture-locking device can include a wedge and a locking nut. In some embodiments, nut is configured to threadably engage the wedge to capture the first suture line and the second suture line within the wedge. The wedge can include a first engagement surface configured to engage a first leaflet of the at least two leaflets and a second engagement surface configured to engage a second leaflet of the at least two leaflets.

In some embodiments, the connector comprises a shape-memory alloy. In some embodiments, the connector is one of a pledgeted suture or a staple. In some embodiments, the implantable prosthetic device includes a first anchor configured to embed into a first valve leaflet and a second anchor configured to embed into a second valve leaflet.

In some implementations, the present disclosure relates to a valve repair system comprising an implantable prosthetic device comprising a first and second paddles that are movable between an open position and a closed position, and a first and second tissue-gripping elements associated with the first and second paddles, respectively, each of the first and second tissue-gripping elements being configured to attach to a respective leaflet of a native heart valve of a patient. The valve repair system further comprises a connector configured to be implanted in first and second leaflets of the native heart valve of the patient when the implantable prosthetic device is gripped to the first and second leaflets and to allow for the implantable prosthetic device to be removed when the connector is implanted in the first and second leaflets, the connector comprising a first anchor configured to engage a first valve leaflet of the native heart valve of the patient, a second anchor configured to engage a second valve leaflet of the native heart valve of the patient, and a connecting portion attached to and extending between the first anchor and the second anchor.

Each of the first and second paddles can comprise an inner paddle portion and an outer paddle portion. In some embodiments, the implantable prosthetic device includes a coaption element. The connector can be configured to keep a gap in the native valve of the patient closed after the prosthetic device is removed. The valve repair system can further comprise two or more additional connectors. The connector can include one or more suture lines.

The connector may include a wedge and a locking nut, the locking nut configured to be attached to the wedge to capture a first suture and a second suture within the wedge. For example, the wedge can include a first engagement surface configured to engage the first valve leaflet and a second engagement surface configured to engage the second valve leaflet. The connector can be one of a pledgeted suture or a staple. In some embodiments, the first anchor is configured to embed into the first valve leaflet and the second anchor is configured to embed into the second valve leaflet.

In some implementations, the present disclosure relates to a method of repairing a heart valve. The method comprises implanting a leaflet-securing implant on first and second leaflets of a native heart valve of a patient, the leaflet-securing implant including two or more leaflet-engagement features configured to hold respective portions of the first and second leaflets in a relatively fixed position. The method further comprises, while the leaflet-securing implant is engaged with the first and second leaflets, implanting an edge-to-edge connector device in the native heart valve of the patient at least in part by engaging a first tissue anchor of the edge-to-edge connector device with the first leaflet and engaging a second tissue anchor of the edge-to-edge connector device with the second leaflet, the second tissue anchor being coupled to the first tissue anchor via one or more connecting sutures. The method further comprises, after implanting the edge-to-edge connector device in the native heart valve, decoupling the leaflet-securing implant from the first and second leaflets, withdrawing the leaflet-securing implant from the heart of the patient, and maintaining the edge-to-edge connector device implanted in the native heart valve.

The leaflet-securing implant can include a spacer configured to occupy at least a portion of a space between respective edges of the first and second leaflets of the native heart valve when the leaflet-securing implant is engaged with the first and second leaflets. In some embodiments, the method further comprises, while the leaflet-securing implant is engaged with the first and second leaflets, implanting one or more additional edge-to-edge connector devices in the native heart valve of the patient. In some embodiments, the first tissue anchor is a first end of a staple device, the second tissue anchor is a second end of the staple device opposite the first end, and the one or more connecting sutures are an intermediate portion of the staple device between the first end and the second end.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures can be drawn to scale for some embodiments, the figures are not necessarily drawn to scale for all embodiments. Embodiments and other features and advantages of the present disclosure will be described and explained with additional specificity and detail through the use of the accompanying drawings in which.

DETAILED DESCRIPTION

Figure 1:
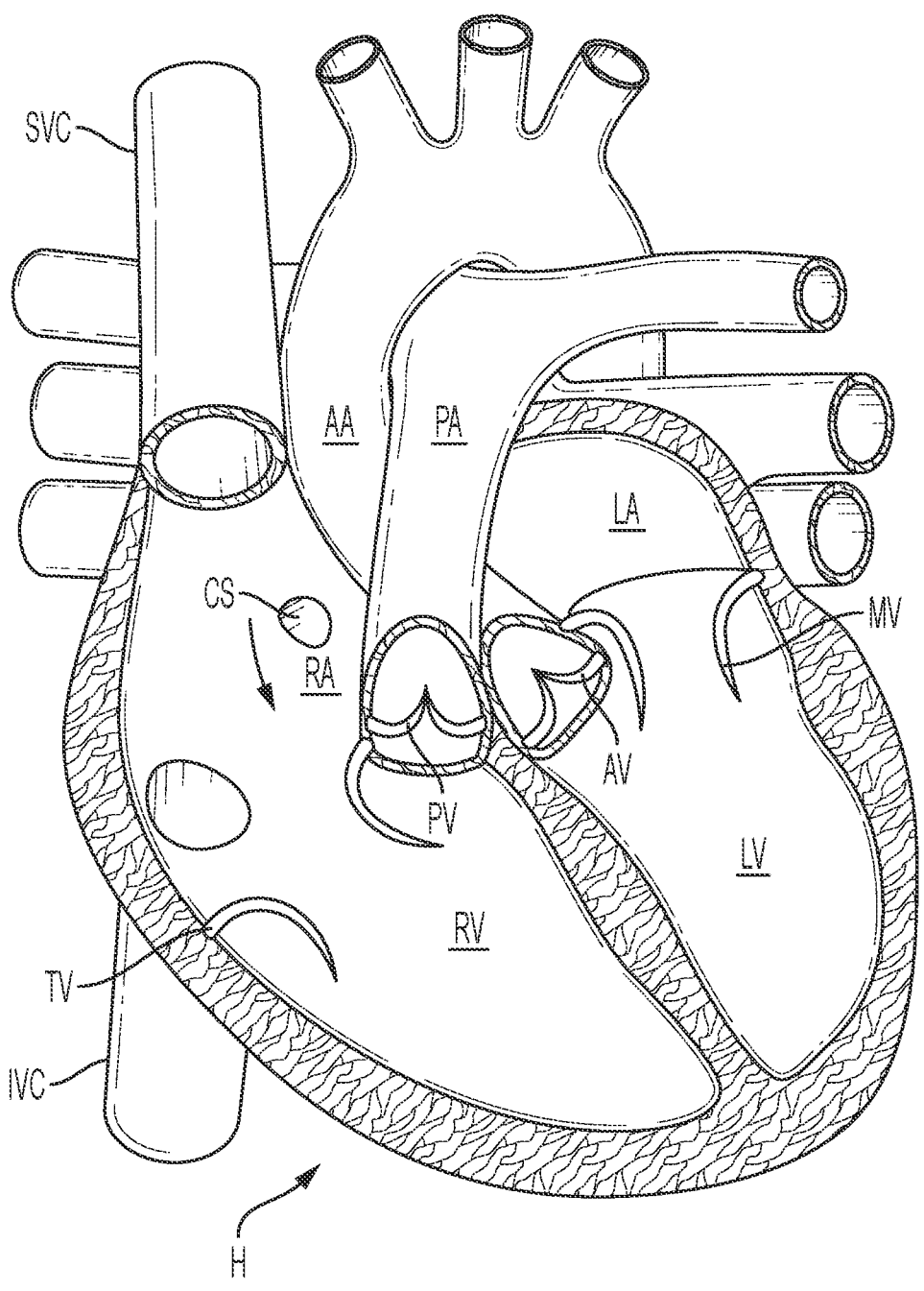
FIG. 1 illustrates a cutaway view of the human heart in a diastolic phase.

The following description refers to the accompanying drawings, which illustrate specific embodiments of the present disclosure. Other embodiments having different structures and operation do not depart from the scope of the present disclosure.

Exemplary embodiments of the present disclosure are directed to systems and methods for repairing a defective heart valve. It should be noted that various embodiments of native valve reparation devices and systems for delivery thereof are disclosed herein, and any combination of these options/features can be made unless specifically excluded. In other words, individual components of the disclosed devices and systems can be combined unless mutually exclusive or otherwise physically impossible.

As described herein, when one or more components are described as being connected, joined, affixed, coupled, attached, or otherwise interconnected, such interconnection may be direct as between the components or may be indirect such as through the use of one or more intermediary components. Also as described herein, reference to a "member," "component," or "portion" shall not be limited to a single structural member, component, or element but can include an assembly of components, members, or elements. Also as described herein, the terms "substantially" and "about" are defined as at least close to (and includes) a given value or state (preferably within 10% of, more preferably within 1% of, and most preferably within 0.1% of).

The native heart valves (i.e., the aortic, pulmonary, tricuspid, and mitral valves) serve critical functions in assuring the forward flow of an adequate supply of blood through the cardiovascular system. These heart valves can be damaged, and thus rendered less effective, by congenital malformations, inflammatory processes, infectious conditions, or disease. Such damage to the valves can result in serious cardiovascular compromise or death. For many years, the definitive treatment for such damaged valves was surgical repair or replacement of the valve during open heart surgery. However, open-heart surgeries are highly invasive and are prone to many complications. Therefore, elderly and frail patients with defective heart valves may not be suitable candidates for open-heart operations. As an alternative, transvascular cardiac operations can be implemented for introducing and implanting prosthetic devices in a manner that is generally much less invasive than open heart surgery. One particular transvascular technique that can be used for accessing the native mitral and aortic valves is the transseptal technique. The transseptal technique can involve inserting a catheter into the right femoral vein, up the inferior vena cava and into the right atrium. The septum is then punctured and the catheter passed into the left atrium. Access to the right atrium can be made via other blood vessels or access points. Furthermore, access to the aortic, tricuspid, mitral, or pulmonary valves in connection with any of the embodiments of the present disclosure can be made using a trans-aortic or trans-apical approach as well.

As described in greater detail below in connection with the description of FIG. 1, a healthy human heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve generally has a different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can generally form a "D"-shaped, oval, or otherwise out-of-round cross-sectional shape having major and minor axes. The anterior leaflet can be larger than the posterior leaflet in some patients, forming a generally "C"-shaped coaptation boundary between the abutting edges of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the edges of the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward/into the left atrium, a plurality of fibrous cords called chordae tendineae tether the leaflets to papillary muscles in the left ventricle.

Mitral regurgitation occurs when the native mitral valve fails to close properly and blood flows into the left atrium from the left ventricle during the systolic phase of heart contraction. Mitral regurgitation is a common form of valvular heart disease. Mitral regurgitation can have different causes, including leaflet prolapse, dysfunctional papillary muscles, or stretching or deformation of the mitral valve annulus resulting from, for example, dilation of the left ventricle. Mitral regurgitation at a central portion of the leaflets can be referred to as central jet mitral regurgitation, whereas mitral regurgitation nearer to one commissure (i.e., location where the leaflets meet) of the leaflets can be referred to as eccentric jet mitral regurgitation. Central jet regurgitation occurs when the edges of the leaflets do not meet in the middle and thus the valve does not close properly, allowing regurgitation to present.

Some solutions for treating mitral regurgitation in patients involve surgically stitching the edges of the native mitral valve leaflets directly to one another at or near a central portion of the leaflet edges, which may be referred to as an Alfieri procedure. Some solutions involve using a catheter delivery system to deliver a clip device to attempt to clip the edges of the leaflets together. However, the use of such clip devices can be associated with certain shortcomings when used to clip the middle of the leaflets where they overlap by about 2 mm or more. Furthermore, the use of multiple clips on the commissures of the mitral valve, where there may be more overlap of the leaflets, can result in a longer operation time and also joins the patient's leaflets at the sides, restricting blood flow. Additionally, both the surgical and clip treatments can create undesirable stress on patient leaflets.

Figure 2:
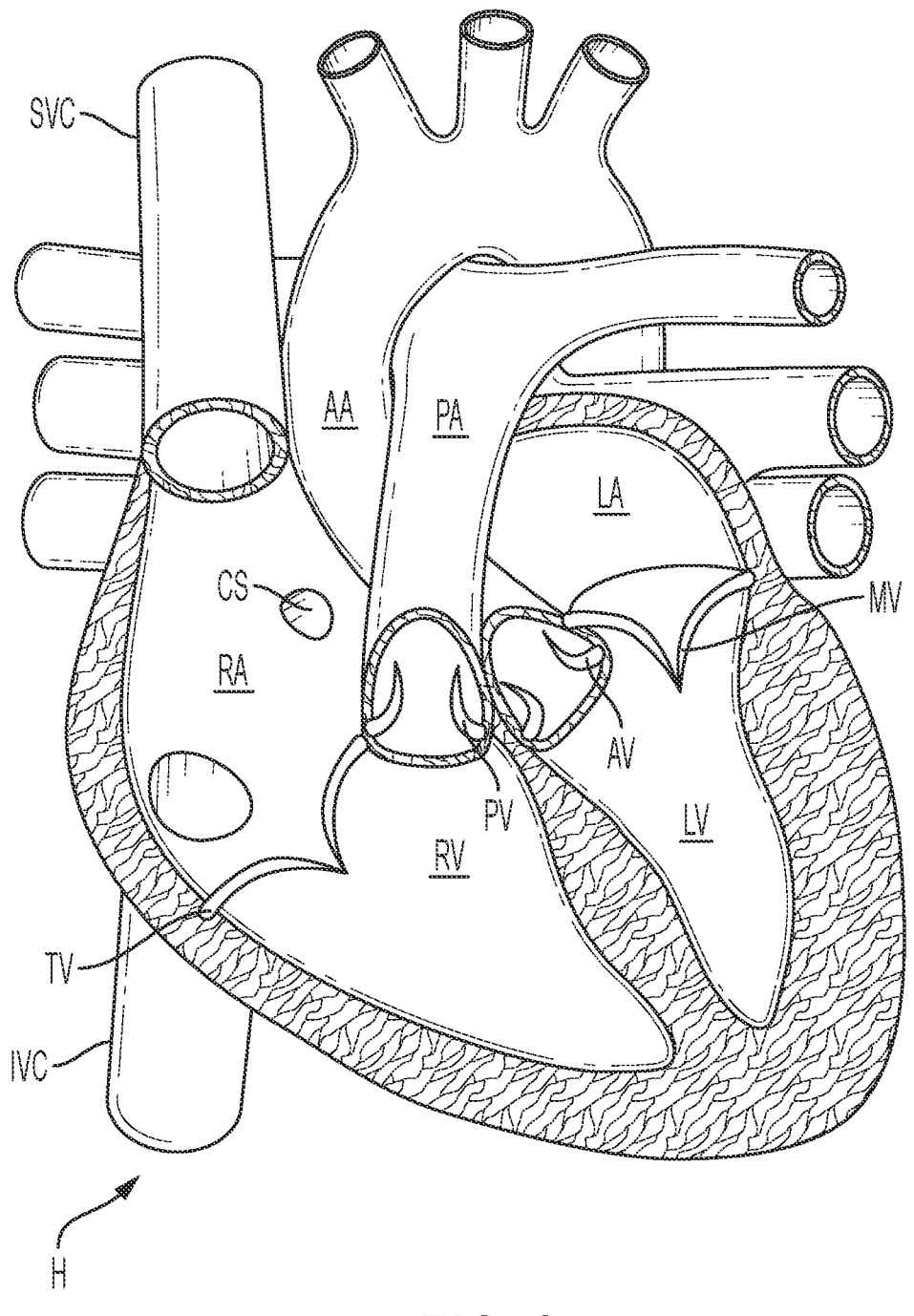
FIG. 2 illustrates a cutaway view of the human heart in a systolic phase.

To provide further context for the inventive solutions disclosed herein, further details of the human cardiac anatomy are disclosed below with reference to FIGS. 1-6. FIGS. 1 and 2 are cutaway views of the human heart H in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta AA, and the pulmonary valve PV separates the right ventricle from the pulmonary artery PA. Each of these valves has flexible leaflets (e.g., leaflets 20, 22 shown in FIGS. 4 and 5) extending inward across the respective orifices that come together or "coapt" in the flowstream to form the one-way, fluid-occluding surfaces. The native valve repair systems of the present application are described primarily with respect to the mitral valve MV. Therefore, anatomical structures of the left atrium LA and left ventricle LV will be explained in greater detail. It should be understood that the devices described herein may also be used in repairing other native valves, e.g., the devices can be used in repairing the tricuspid valve TV, the aortic valve AV, and the pulmonary valve PV.

The left atrium LA receives oxygenated blood from the lungs. During the diastolic phase, or diastole, seen in FIG. 1, the blood that was previously collected in the left atrium LA (during the systolic phase) moves through the mitral valve MV and into the left ventricle LV by expansion of the left ventricle LV. In the systolic phase, or systole, seen in FIG. 2, the left ventricle LV contracts to force the blood through the aortic valve AV and ascending aorta AA into the body. During systole, the leaflets of the mitral valve MV close to prevent the blood from regurgitating from the left ventricle LV and back into the left atrium LA, and blood is collected in the left atrium from the pulmonary vein. In one exemplary embodiment, the systems and devices described by the present application are used to repair the function of a defective mitral valve MV. That is, the systems and devices are configured to help close the leaflets of the mitral valve to prevent blood from regurgitating from the left ventricle LV and back into the left atrium LA.

Figure 3:
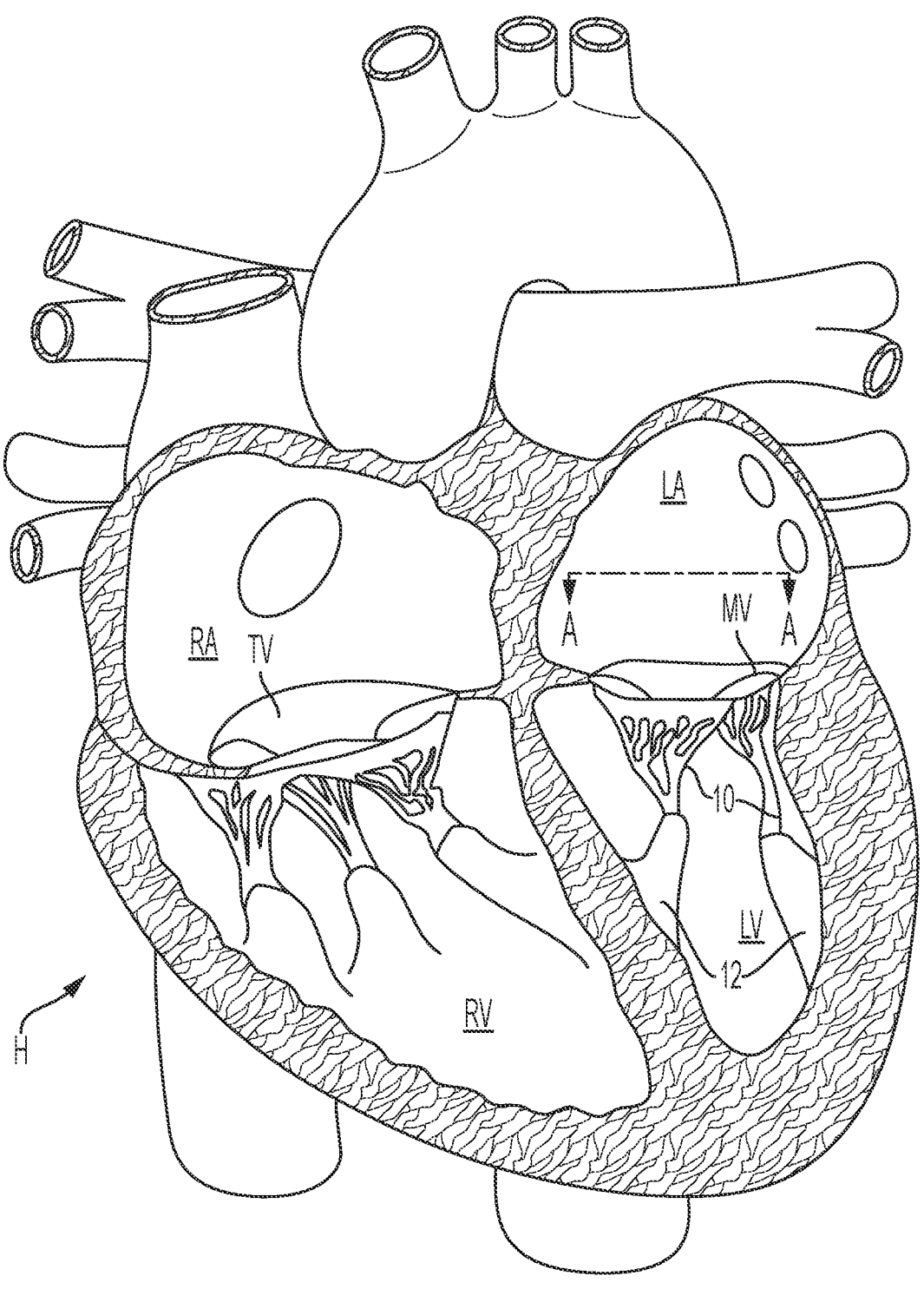
FIG. 3 illustrates a cutaway view of the human heart in a diastolic phase, in which the chordae tendineae are shown attaching the leaflets of the mitral and tricuspid valves to ventricle walls.

Referring now to FIGS. 1-6, the mitral valve MV includes two leaflets, the anterior leaflet 20 and the posterior leaflet 22. The mitral valve MV also includes an annulus 24, which is a variably dense fibrous ring of tissues that encircles the leaflets 20, 22. Referring to FIG. 3, the mitral valve MV is anchored to the wall of the left ventricle LV by chordae tendineae 10. The chordae tendineae 10 are cord-like tendons that connect the papillary muscles 12 (i.e., the muscles located at the base of the chordae tendineae and within the walls of the left ventricle) to the leaflets 20, 22 of the mitral valve MV. The papillary muscles 12 serve to limit the movements of the mitral valve MV and prevent the mitral valve from being reverted. The mitral valve MV opens and closes in response to pressure changes in the left atrium LA and the left ventricle LV. The papillary muscles do not open or close the mitral valve MV. Rather, the papillary muscles brace the mitral valve MV against the high pressure needed to circulate blood throughout the body. Together the papillary muscles and the chordae tendineae are known as the subvalvular apparatus, which functions to keep the mitral valve MV from prolapsing into the left atrium LA when the mitral valve closes.

Various disease processes can impair proper function of one or more of the native valves of the heart H. These disease processes include degenerative processes (e.g., Barlow's Disease, fibroelastic deficiency), inflammatory processes (e.g., Rheumatic Heart Disease), and infectious processes (e.g., endocarditis). In addition, damage to the left ventricle LV or the right ventricle RV from prior heart attacks (i.e., myocardial infarction secondary to coronary artery disease) or other heart diseases (e.g., cardiomyopathy) can distort a native valve's geometry, which can cause the native valve to dysfunction. However, the vast majority of patients undergoing valve surgery, such as surgery to the mitral valve MV, suffer from a degenerative disease that causes a malfunction in a leaflet (e.g., leaflets 20, 22) of a native valve (e.g., the mitral valve MV), which results in prolapse and regurgitation.

Generally, a native valve may malfunction in two different ways: (1) valve stenosis; and (2) valve regurgitation. Valve stenosis occurs when a native valve does not open completely and thereby causes an obstruction of blood flow. Typically, valve stenosis results from buildup of calcified material on the leaflets of a valve, which causes the leaflets to thicken and impairs the ability of the valve to fully open to permit forward blood flow.

The second type of valve malfunction, valve regurgitation, occurs when the leaflets of the valve do not close completely thereby causing blood to leak back into the prior chamber (e.g., causing blood to leak from the left ventricle to the left atrium). There are three mechanisms by which a native valve becomes regurgitant—or incompetent—which include Carpenter's type I, type II, and type III malfunctions. A Carpentier type I malfunction involves the dilation of the annulus such that normally functioning leaflets are distracted from each other and fail to form a tight seal (i.e., the leaflets do not coapt properly). Included in a type I mechanism malfunction are perforations of the leaflets, as are present in endocarditis. A Carpentier's type II malfunction involves prolapse of one or more leaflets of a native valve above a plane of coaption. A Carpentier's type III malfunction involves restriction of the motion of one or more leaflets of a native valve such that the leaflets are abnormally constrained below the plane of the annulus. Leaflet restriction can be caused by rheumatic disease (Ma) or dilation of a ventricle (IIIb).

Figure 4:
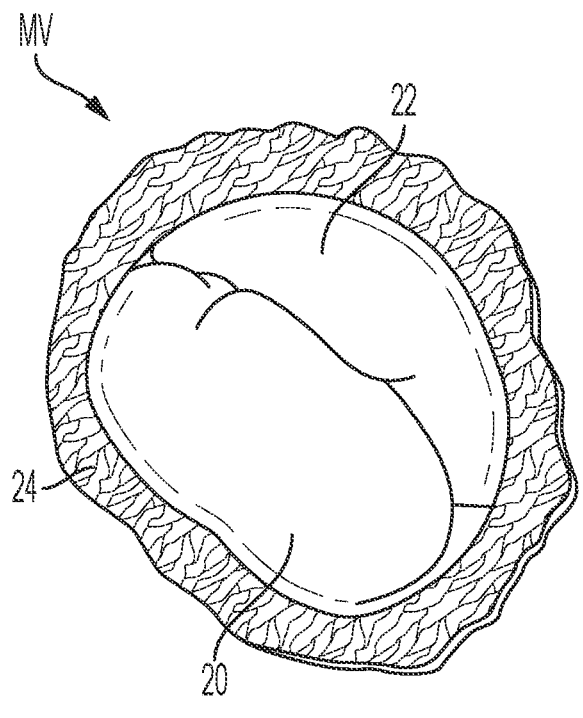
FIG. 4 illustrates a healthy mitral valve with the leaflets closed as viewed from an atrial side of the mitral valve.
Figure 5:
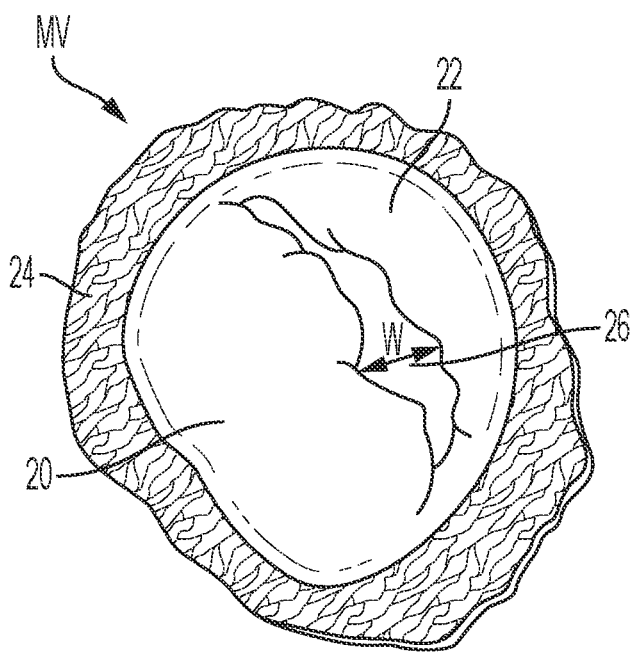
FIG. 5 illustrates a dysfunctional mitral valve with a visible gap between the leaflets as viewed from an atrial side of the mitral valve.

Referring to FIG. 4, when a healthy mitral valve MV is in a closed position, the anterior leaflet 20 and the posterior leaflet 22 coapt, which prevents blood from leaking from the left ventricle LV to the left atrium LA. Referring to FIG. 5, regurgitation occurs when the anterior leaflet 20 or the posterior leaflet 22 of the mitral valve MV is displaced into the left atrium LA during systole. This failure to coapt causes a gap 26 between the anterior leaflet 20 and the posterior leaflet 22, which allows blood to flow back into the left atrium LA from the left ventricle LV during systole. As set forth above, there are several different ways that a leaflet (e.g. leaflets 20, 22 of mitral valve MV) may malfunction, which can thereby lead to regurgitation.

Referring to FIG. 5, in certain situations, the mitral valve MV of a patient can have a wide gap 26 between the anterior leaflet 20 and the posterior leaflet 22 when the mitral valve is in a closed position (i.e., during the systolic phase). For example, the gap 26 can have a width W between about 2.5 mm and about 17.5 mm, such as between about 5 mm and about 15 mm, such as between about 7.5 mm and about 12.5 mm, such as about 10 mm. In some situations, the gap 26 can have a width W greater than 15 mm. In any of the above-mentioned situations, a valve repair system is desired that is capable of engaging the anterior leaflet 20 and the posterior leaflet 22 to close the gap 26 and prevent regurgitation of blood through the mitral valve MV.

Although stenosis or regurgitation can affect any valve, stenosis is predominantly found to affect either the aortic valve AV or the pulmonary valve PV, and regurgitation is predominantly found to affect either the mitral valve MV or the tricuspid valve TV. Both valve stenosis and valve regurgitation increase the workload of the heart H and may lead to very serious conditions if left un-treated; such as endocarditis, congestive heart failure, permanent heart damage, cardiac arrest, and ultimately death. Because the left side of the heart (i.e., the left atrium LA, the left ventricle LV, the mitral valve MV, and the aortic valve AV) is primarily responsible for circulating the flow of blood throughout the body, malfunction of the mitral valve MV or the aortic valve AV is particularly problematic and often life threatening. Accordingly, because of the substantially higher pressures on the left side of the heart, dysfunction of the mitral valve MV or the aortic valve AV is much more problematic.

Malfunctioning native heart valves may either be repaired or replaced. Repair typically involves the preservation and correction of the patient's native valve. Replacement typically involves replacing the patient's native valve with a biological or mechanical substitute. Typically, the aortic valve AV and pulmonary valve PV are more prone to stenosis. Because stenotic damage sustained by the leaflets is irreversible, the most conventional treatments for a stenotic aortic valve or stenotic pulmonary valve are removal and replacement of the valve with a surgically implanted heart valve, or displacement of the valve with a transcatheter heart valve. The mitral valve MV and the tricuspid valve TV are more prone to deformation of leaflets, which, as described above, prevents the mitral valve or tricuspid valve from closing properly and allows for regurgitation or back flow of blood from the ventricle into the atrium (e.g., a deformed mitral valve MV may allow for regurgitation or back flow from the left ventricle LV to the left atrium LA). The regurgitation or back flow of blood from the ventricle to the atrium results in valvular insufficiency. Deformations in the structure or shape of the mitral valve MV or the tricuspid valve TV are often repairable. In addition, regurgitation can occur due to the chordae tendineae 10 becoming dysfunctional (e.g., the chordae tendineae may stretch or rupture), which allows the anterior leaflet 20 and the posterior leaflet 22 to be reverted such that blood is regurgitated into the left atrium LA. The problems occurring due to dysfunctional chordae tendineae 10 can be repaired by repairing the chordae tendineae or the structure of the mitral valve (e.g., by securing the leaflets 20, 22 at the affected portion of the mitral valve).

Figure 6:
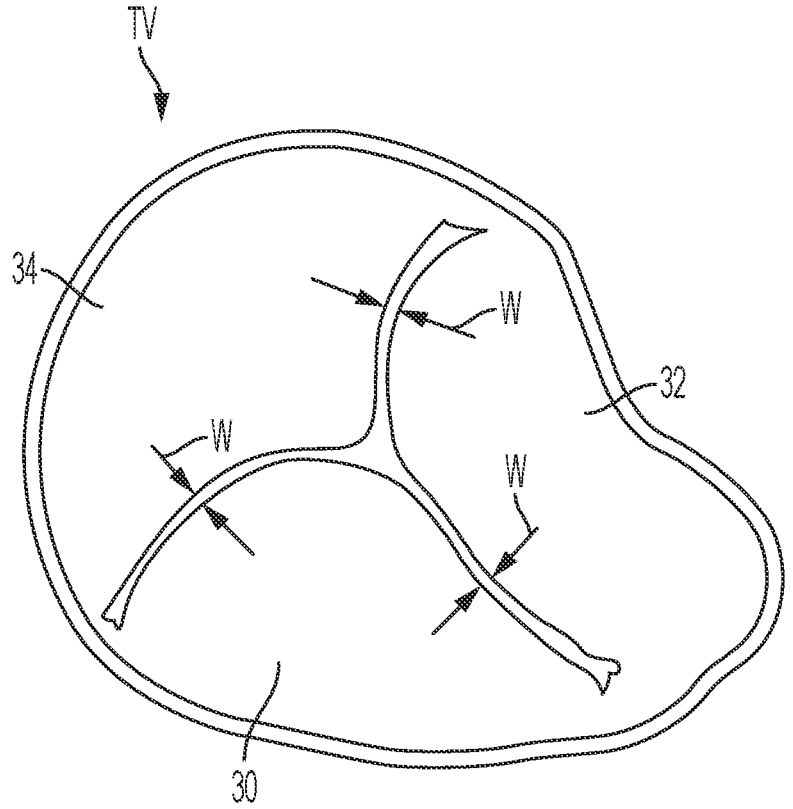
FIG. 6 illustrates a tricuspid valve viewed from an atrial side of the tricuspid valve.

The systems and procedures disclosed herein refer to repairing the structure of a mitral valve. However, it should be understood that the systems, devices, and concepts provided herein can be used to repair any native valve, as well as any component of a native valve. Referring now to FIG. 6, any of the devices and concepts provided herein can be used to repair the tricuspid valve TV. For example, any of the systems, devices, methods, and concepts provided herein can be used between any two of the anterior leaflet 30, septal leaflet 32, and posterior leaflet 34 of the tricuspid valve TV to prevent regurgitation of blood from the right ventricle into the right atrium. In addition, any of the systems, devices, methods, and concepts provided herein can be used on all three of the leaflets 30, 32, 34 together to prevent regurgitation of blood from the right ventricle to the right atrium. That is, the valve repair systems provided herein can be centrally located between the three leaflets 30, 32, 34.

Some embodiments of systems for repairing a mitral or tricuspid valve in accordance with the present disclosure include a connector or an implantable prosthetic device. The connector and implantable prosthetic device can take a wide variety of different forms. For example, the implantable prosthetic device can be any device which holds a portion of the valve leaflets while the connector is implanted and that can be either removed (leaving the connector installed/implanted on the valve leaflets) or left installed/implanted on the native valve leaflets with the connector. For example, in some embodiments, an implantable prosthetic device can have an optional coaption element and at least one anchor for permanently or temporarily attaching to a valve leaflet. The optional coaption element can be configured to be positioned or disposed within the native heart valve orifice to at least partially fill the space between the valve leaflets or to form a more effective seal, thereby reducing or preventing regurgitation. The coaption element can be reduced in size or eliminated or omitted in certain embodiments disclosed herein, wherein the implantable prosthetic device may be removed after the connector is implanted. When included, the coaption element can have a structure that is impervious to blood and that allows the native leaflets to close around at least a portion of the coaption element during ventricular systole to block at least an amount of blood from flowing from the left or right ventricle back into the left or right atrium, respectively. The prosthetic device can be configured to seal against two or three native valve leaflets; that is, the device may be used in the native mitral (bicuspid) or tricuspid valves. The coaption element is sometimes referred to herein as a "spacer" because the coaption element can fill a space between improperly functioning native mitral or tricuspid leaflets that do not close/coapt completely.

The optional coaption element can have various shapes. In some embodiments, the coaption element can have an elongated cylindrical shape having an at least partially round cross-sectional shape. In some embodiments, the coaption element can have an oval cross-sectional shape, a crescent cross-sectional shape, or various other non-cylindrical shapes. When the prosthetic device is attached to the native valve leaflets, the coaption element can include an atrial portion positioned in or adjacent to the left atrium, a ventricular or lower portion positioned in or adjacent to the left ventricle, and a side surface that extends between the native mitral leaflets. In embodiments configured for use in the tricuspid valve, the atrial or upper portion can be positioned in or adjacent to the right atrium and the ventricular or lower portion can be positioned in or adjacent to the right ventricle, wherein the side surface extends between the native tricuspid leaflets.

The anchor component(s) of the prosthetic device can be configured to secure the device to one or both of the native mitral leaflets such that the coaption element is positioned between the two native leaflets. In embodiments configured for use in the tricuspid valve, the anchor can be configured to secure the device to one, two, or three of the tricuspid leaflets, such that the coaption element is positioned between two or three of the native leaflets. In some embodiments, the anchor can attach to the coaption element at a location adjacent to or associated with the ventricular portion of the coaption element. In some embodiments, the anchor can be coupled/attached to a shaft or actuation wire, to which the coaption element is also attached. In some embodiments, the anchor and the coaption element can be positioned independently with respect to each other by separately moving each of the anchor and the coaption element along the longitudinal axis of the shaft or actuation wire. In some embodiments, the anchor and the coaption element can be positioned simultaneously by moving the anchor and the coaption element together along the longitudinal axis of the shaft or actuation wire. The anchor can be configured to be positioned behind, at least in part, a native leaflet when implanted such that the leaflet is grasped by the anchor or pinned or captured between the anchor and the coaptation element.

The prosthetic device can be configured to be implanted via a delivery sheath/catheter. The optional coaption element and the anchor can be compressible to a radially compressed state and can be self-expandable to a radially expanded state when compressive pressure is released or when the various components are manually expanded. The prosthetic device can be configured for the anchor to be expanded radially away from the still-compressed coaption element initially in order to create a gap between the coaption element and the anchor. A native leaflet can then be positioned in the gap. The coaption element can be expanded radially, closing the gap between the coaption element and the anchor and capturing the leaflet between the coaption element and the anchor. In some embodiments, the anchor and coaption element are configured to self-expand. The implantation methods for various embodiments can be different and are more fully discussed below with respect to each embodiment. Additional information regarding these and other delivery methods can be found in U.S. Pat. No. 8,449,599 and U.S. Patent Application Publication Nos. 2014/0222136, and 2014/0067052, 2016/0331523 each of which is incorporated herein by reference in its entirety. U.S. Provisional Patent Application No. 62/744,031, filed Oct. 10, 2018, entitled Heart Valve Sealing Devices and Delivery Devices Therefor, discloses an exemplary implantable prosthetic device, the disclosure of which is incorporated herein by reference in its entirety.

The disclosed prosthetic devices can be configured such that the anchor component is connected to one or more leaflets, thereby taking advantage of the tension from native chordae tendineae to resist high systolic pressure urging the device toward the left atrium. During diastole, the devices can rely on the compressive and retention forces exerted on the leaflet that is grasped by the anchor(s).

Deployable and releasable prosthetic devices, including but not limited to the disclosed deployable and releasable prosthetic devices, can be configured as part of a valve repair system that is used in conjunction with one or more connectors (e.g., sutures) that connect the leaflets of the heart valve together. The connectors can be configured in a variety of ways. For example, each of the one or more connectors may be a suture, a staple, a stitch/suture, or other suitable connector. The connectors may be separate from, or connected but separable from, the prosthetic device. The disclosed prosthetic device may be configured to grasp one or more leaflets of the heart valve to hold the heart valve (or portions of the heart valve, such as leaflets) in a position while the one or more connectors are being attached to the leaflets. Once the one or more connectors are in place and connecting the leaflets of the heart valve together, the implantable prosthetic device may be kept in position and used in combination with the one or more connectors, or the implantable prosthetic device may be released and removed from the heart while the connectors remain in position.

The terms "suture" and "stitch" are used herein according to their broad/plain and ordinary meaning and may refer to any elongate cord strip, strand, line, rope, wire, filament, tie, string, ribbon, strap, or portion thereof, or other type/form of material used in medical procedures (e.g., ePTFE suture, for example, GORE-TEX® sutures, W. L. Gore, Newark, Delaware). Furthermore, embodiments of the present disclosure may be implemented in connection with non-surgical or non-biological suture or stich implantation. With respect to the present disclosure, one having ordinary skill in the art will understand that a wire, staple, or other similar material may be used in place of a suture/stitch. Furthermore, in some contexts herein, the terms "stitch" and "suture" may be used substantially interchangeably. In addition, use of the singular form of any of the suture-related terms listed above, including the terms "suture" and "stitch," may be used to refer to a single suture/cord, or to a portion thereof. Furthermore, sutures/stitches may be used with a pledget to reduce tissue damage or spread the suture or stitch load over a broader surface area.

The implantation methods for various embodiments of the disclosed prosthetic devices and the configuration of the disclosed prosthetic devices can be adapted to both allow for deployment and, in some cases, release of the prosthetic devices as well as the deployment and attachment of the one or more connectors to the leaflets of the heart valve after deployment of the prosthetic devices.

Referring now to FIGS. 7-12, an exemplary embodiment of an implantable prosthetic device 100 is shown being delivered and implanted within the native mitral valve MV of the heart H. As with the implantable device disclosed in detail in U.S. Provisional Patent Application No. 62/744, 031, the implantable prosthetic device 100 may be deployed from a delivery sheath or means for delivery 102 and optionally includes a coaption portion 104 and an anchor portion 106. The coaption portion/element is optional or may be minimized in size in the present application, since the prosthetic device may be removed, and thus the coaptation portion would not serve to improve leaflet coaptation postoperatively and the utility thereof is reduced compared to implementations in which the prosthetic device remains implanted in the patient post-operatively. The coaption portion 104 of the implantable prosthetic device 100 includes a coaption element or means for coapting 110 that is adapted to be implanted between the leaflets of the native mitral valve and may be slidably attached to an actuation wire or shaft 112 during one or more periods of the process.

The prosthetic device 100 may be considered a leaflet-securing implant due to its ability to clamp, grip, hold, clip, pinch, or otherwise secure portions of two or more leaflets thereto, thereby maintaining a fixed relative position of such leaflet portions. The device 100 may be a clip device or may include a central spacer element or portion in some embodiments, while other embodiments may omit such features. The prosthetic device 100 may further be considered an edge-to-edge repair device in that it is configured to attach to or between the edges of the target valve leaflets or repair or compensate for a gap that may undesirably form or exist between the edges of the native valve leaflets.

In some embodiments, the overall shape of the coaption element or means for coapting 110 is an elliptical or oval cross section when seen from the surgeon's view (top view), a tapered shape or cross section when seen from an LVOT view (side view), and a substantially round shape or rounded shape when seen from an intra-commissural view. In some embodiments, a blend of these three geometries can result in the three-dimensional shape of the illustrated coaption element or means for coapting 110.

The anchor portion 106 can be actuatable between open and closed conditions/configurations and can take a wide variety of forms, such as, for example, paddles, gripping elements, or the like. Actuation of the actuation wire or means for actuating 112 can open or close the anchor portion 106 of the implantable prosthetic device 100 to grasp the mitral valve leaflets during implantation.

Figure 9:
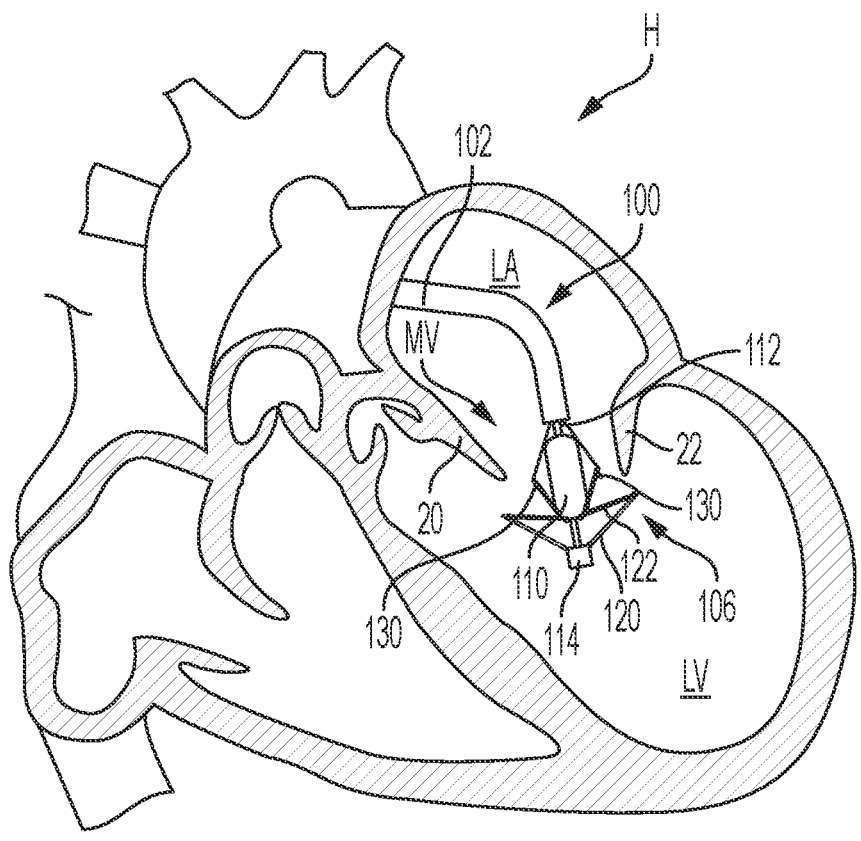

Referring to FIG. 9, in the illustrated embodiment, the anchor portion 106 of the implantable prosthetic device 100 includes outer paddles 120 and inner paddles 122 that may be connected between a cap 114 and the distal end of the coaption element or means for coapting 110. The anchor portion 106 further includes attachment portions or gripping members. The illustrated gripping members can comprise barbed clasps 130 that can be opened separately by pulling on an attached actuation line 116 that extends through the delivery sheath or means for delivery 102 to the barbed clasp 130.

The coaption element or means for coapting 110 and paddles 120, 122 can be formed from a flexible material that may be a metal fabric, such as a mesh, woven, braided, or formed in any other suitable way or a laser cut or otherwise cut flexible material. The flexible material may be cloth, shape-memory alloy wire—such as Nitinol—to provide shape-setting capability, or any other flexible material suitable for implantation in the human body.

Figure 7:
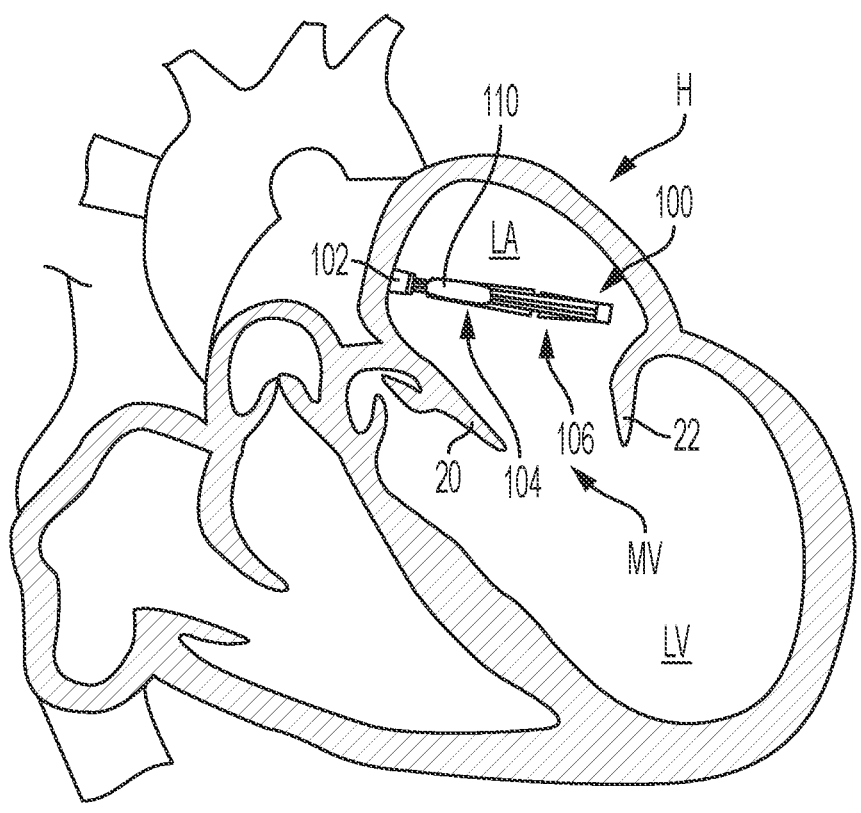
FIGS. 7-12 show an exemplary embodiment of an implantable prosthetic device being delivered and implanted within the native mitral valve.
Figure 8:
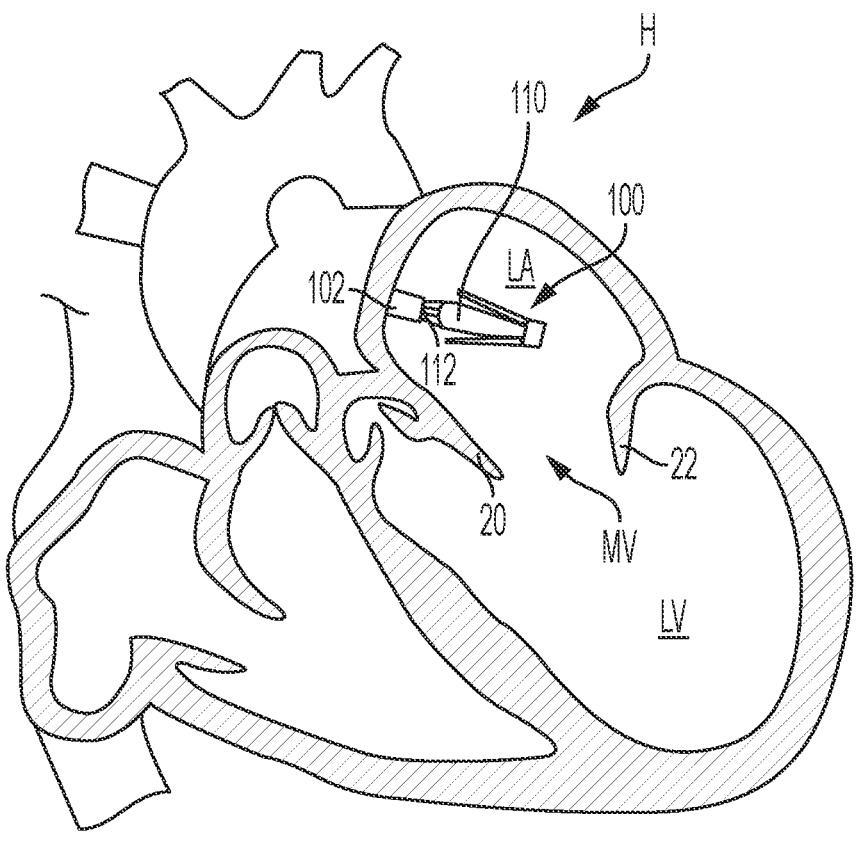

Referring now to FIG. 7, the delivery sheath or means for delivery 102 (e.g., catheter delivery system) is inserted into the left atrium LA, for example, through the septum, and the implantable prosthetic device 100 is deployed from the delivery sheath or means for delivery 102 in an open (e.g., fully open) condition/configuration. The actuation wire or means for actuating 112 can then be retracted to move the implantable prosthetic device 100 into an at least partially closed (e.g., fully closed) condition/configuration, as shown in FIG. 8.

Figure 10:
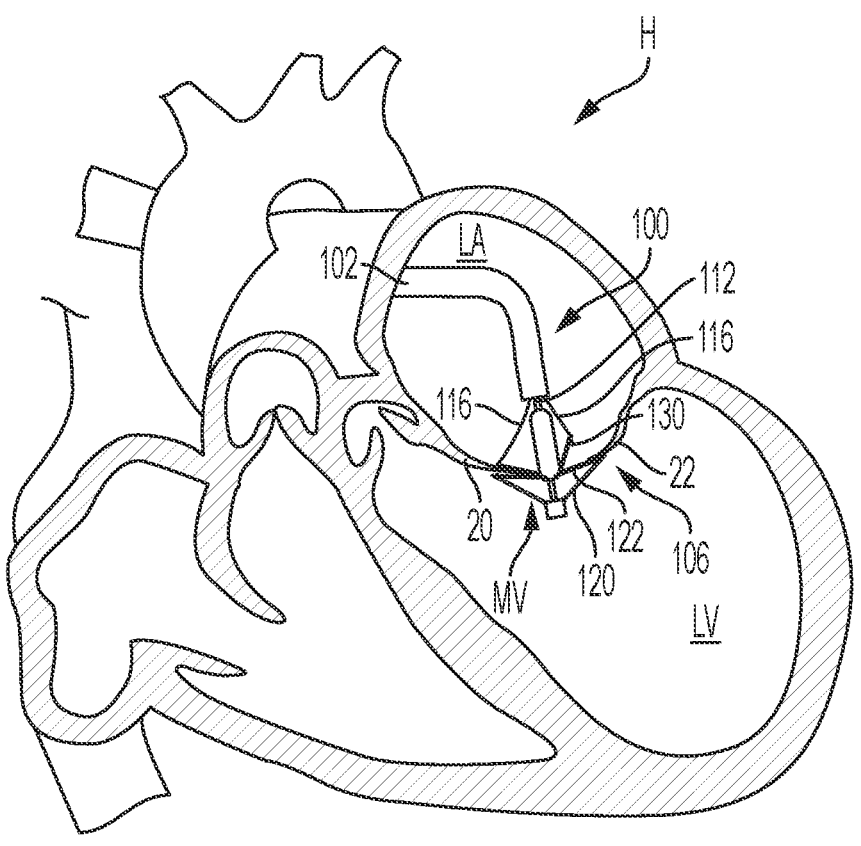
Figure 11:
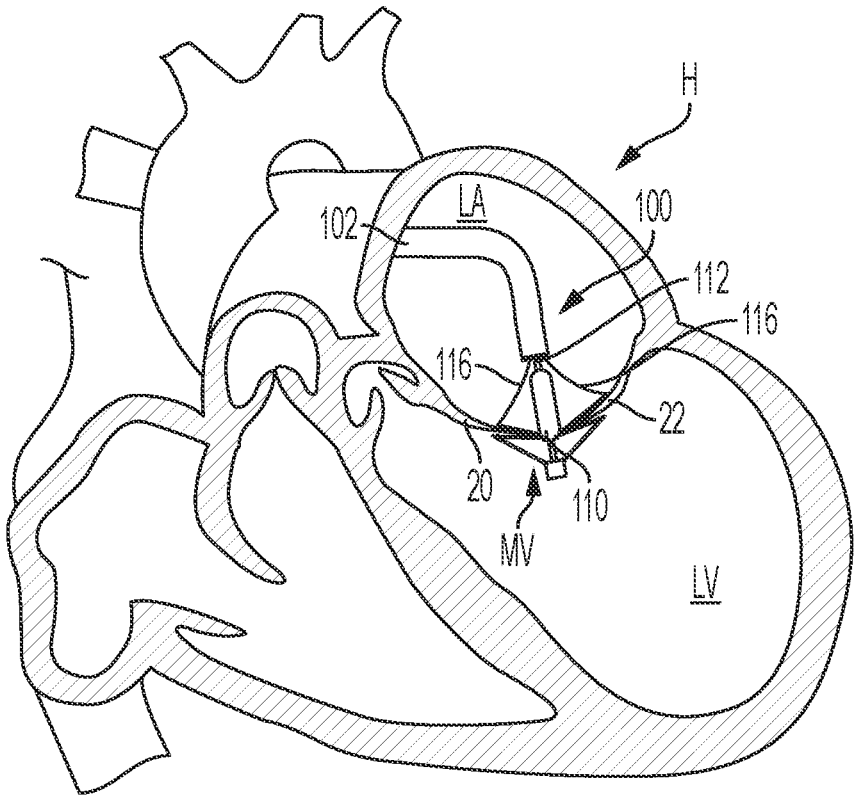
Figure 12:
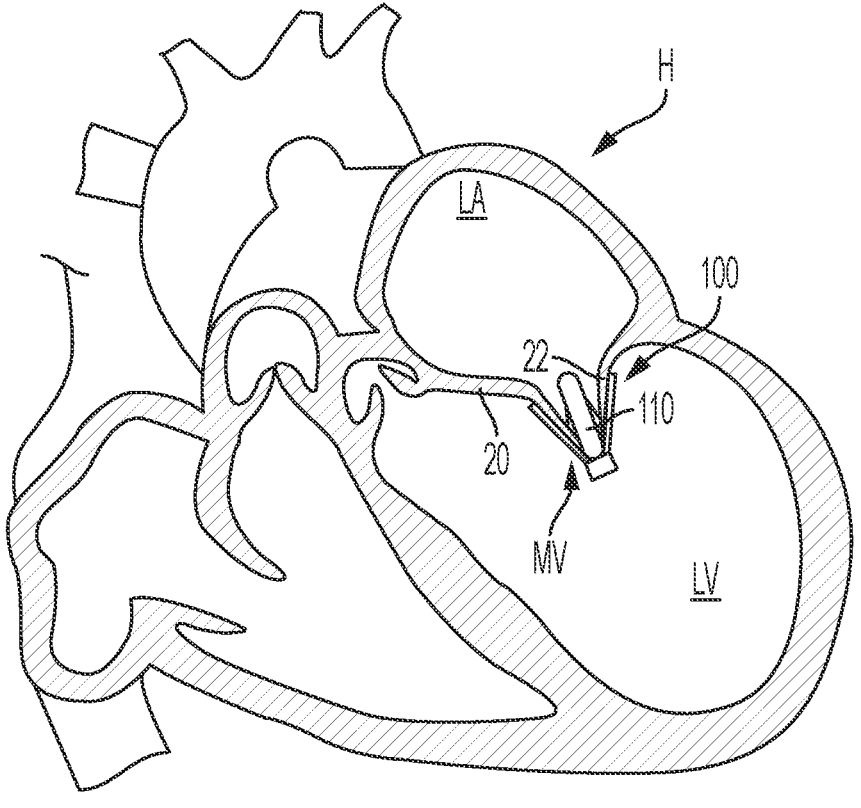

As can be seen in FIG. 9, the implantable prosthetic device 100 can be moved into a position at least partially within the mitral valve MV, into the ventricle LV, and at least partially opened so that the leaflets 20, 22 can be grasped. Referring now to FIG. 10, an actuation line 116 can be extended to close one of the clasps 130, capturing the valve leaflet 20. FIG. 11 shows another actuation line 116 being extended to close the other clasp 130, capturing the remaining leaflet 22. As can be seen in FIG. 12, one or more of the delivery sheath or means for delivery 102, the actuation wire or means for actuating 112, and the actuation line(s) 116 can then be retracted, in some implementations, and the implantable prosthetic device 100 can be left in place fully closed and deployed in the native mitral valve MV.

As shown in FIGS. 13-18, the implantable prosthetic device 100 can facilitate one or more connectors (e.g., sutures) 140 being deployed and implanted to connect the two valve leaflets 20, 22 together while the implantable prosthetic device 100 is in place. The one or more connectors 140 can be attached to the leaflets 20, 22 and left in place along with the fully closed and implantable prosthetic device 100 or the one or more connectors 140 can be attached to the leaflets 20, 22 and left in place and the implantable prosthetic device 100 can be released and removed along with the delivery sheath or means for delivery 102, the actuation wire or means for actuating 112, or the actuation line(s) 116. The connector 140 can be considered an edge-to-edge valve repair device because it is configured to be coupled to or approximate the edges of two or more leaflets to one another to thereby reduce a gap that may otherwise present/exist between the edges of the native valve leaflets.

Figure 13:
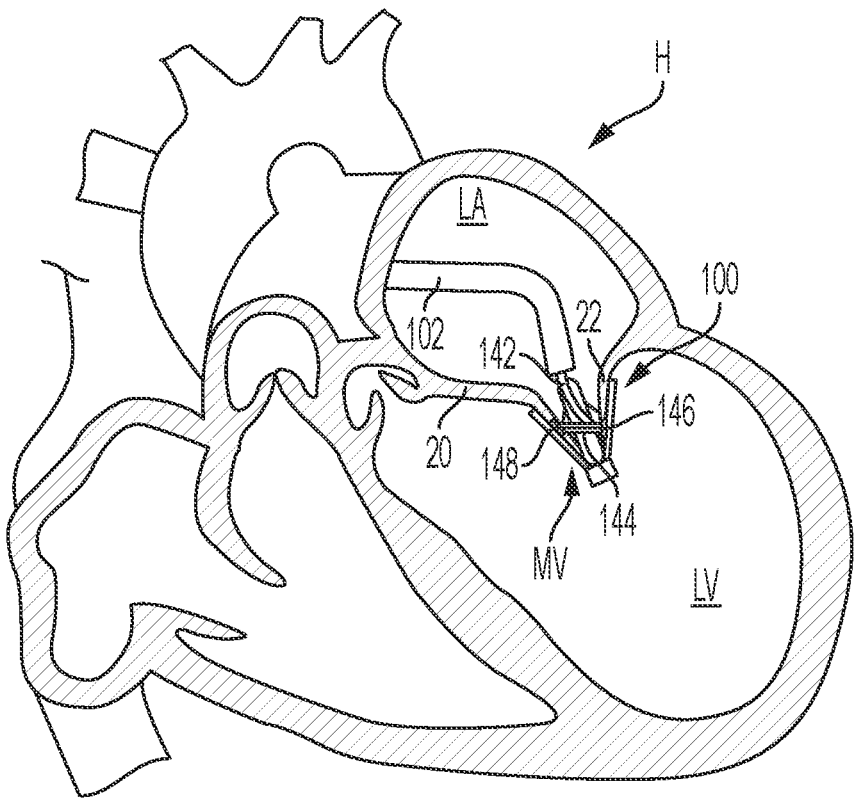
FIGS. 13-18 shows the implantable prosthetic device of FIGS. 7-12 applying a suture and removing the device.

Referring to FIG. 13, in the illustrated embodiment, the clasps 130 on the implantable prosthetic device 100 have been closed to capture the valve leaflets 20, 22, respectively, while the delivery sheath or means for delivery 102 or the actuation wire or means for actuating 112 have not been retracted. In some implementations, a secondary delivery sheath or secondary means for deliver (e.g., catheter delivery system) 142 may have been deployed through the delivery sheath or means for delivery 102 to deploy the one or more connectors 140. In some embodiments, the secondary delivery sheath or secondary means for delivery 142 includes an open distal end 144 and may be steerable such that the distal end 144 can be positioned as desired, such as adjacent a valve leaflet 20, 22 as shown in FIG. 13.

The one or more connectors 140 can be deployed through the secondary delivery sheath or secondary means for delivery 142 (or through any other delivery system or mechanism). The one or more connectors 140 can be configured in a variety of ways. Any suitable connector or connecting means 140 capable of being deployed through a delivery sheath or a catheter and able to connect the valve leaflets 20, 22 together may be used. For example, the connector or connecting means 140 may be a suture, a pledgeted suture, a staple, a stitch, a wire, or other suitable connecting device.

Figure 15:
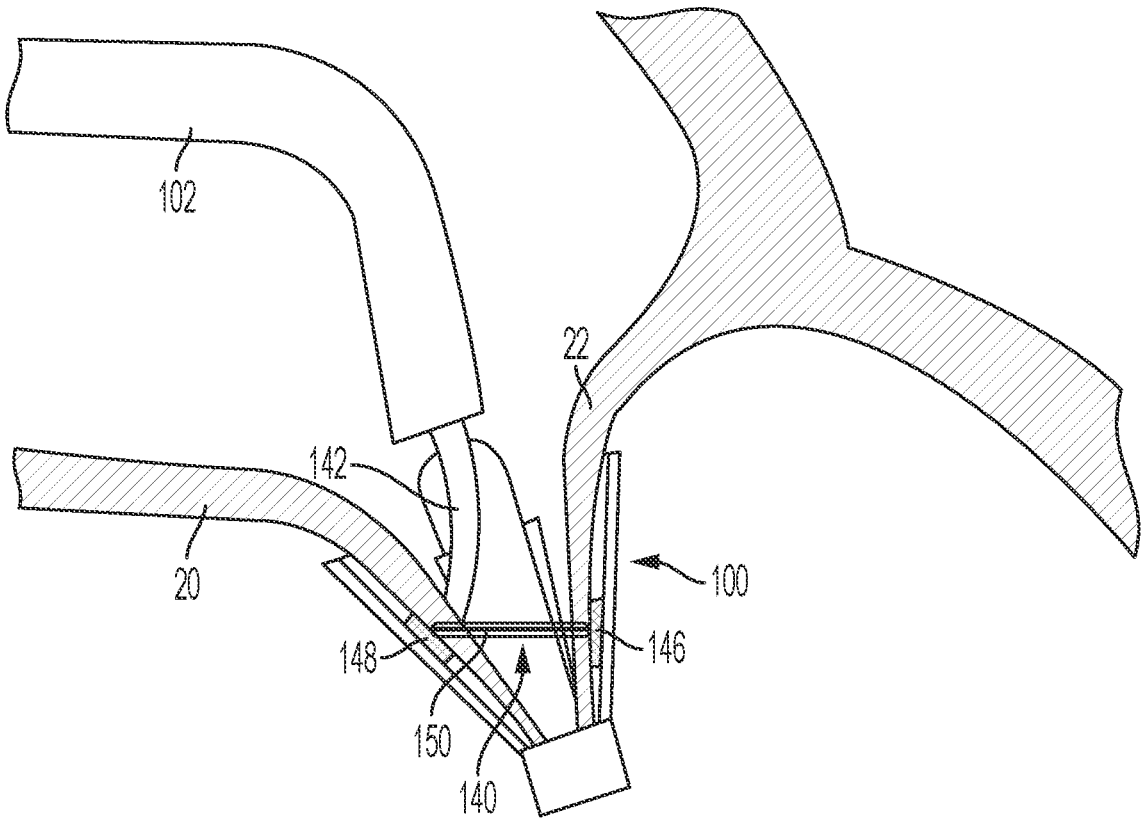

As best illustrated in FIG. 15, in the illustrated embodiment, the connector 140 includes a first tissue anchor 146 positioned on the ventricular side of the second valve leaflet 22 and a second tissue anchor 148 positioned on the ventricular side of the first valve leaflet 20. The first anchor 146 and the second anchor 148 are connected to each other, through the leaflets 20, 22, by a connecting portion. In the illustrated embodiment, the connecting portion is a suture line 150.

Referring to FIG. 13, with the distal end 144 of the secondary delivery sheath or secondary means for delivery 142 positioned adjacent the atrial side of the second valve leaflet 22, the second valve leaflet 22 may be pierced to create an opening (not shown) therein. The second valve leaflet 22 may be pierced in any of a variety of ways. For example, a piercing device (not shown), such as a needle or other pointed-tip or sharp-edged device may be delivered through the secondary delivery sheath or secondary means for delivery 142 to the distal end 144 and extended or pushed through the second valve leaflet 22. Alternatively, the distal end 144 of the secondary delivery sheath or secondary means for delivery 142 may be adapted to pierce the valve leaflet 22. For example, the distal end 144 of the delivery sheath may be sharp or pointed, like a needle, but may also include a lumen for delivering the catheter.

Once the second valve leaflet 22 has been pierced, the connector 140 may be delivered through the secondary delivery sheath or secondary means for delivery 142 to the distal end 144 and extended or pushed through the opening in the second valve leaflet 22. In the illustrated embodiment, the first anchor 146 is attached to, or formed at, the end of the suture line 150. The first anchor may be attached to, or formed at, the end of the suture line 150 while both the suture line 150 and the first anchor 146 are delivered through the secondary delivery sheath or secondary means for delivery 142. In other embodiments, the first anchor 146 may be attached to, or formed in, the end of the suture line 150 after the suture line 150 is delivered through the secondary delivery sheath or secondary means for delivery 142.

The first anchor 146 may be configured in a variety of ways. Any configuration that can be positioned adjacent the second valve leaflet 22 to secure the suture line 150 to the second valve leaflet 22 may be used. For example, the first anchor 146 can be a pledget, a knot formed in the suture line 150, a stop, or other suture line anchoring device. The first anchor 146 may be collapsible/expandable such that within the secondary delivery sheath or secondary means for delivery 142, the first anchor 146 is in a collapsed state. Once the first anchor 146 exits the distal end 144 of the secondary delivery sheath or secondary means for delivery 142, the first anchor 146 may expand. In one exemplary embodiment, the first anchor 146 includes a shape-memory alloy wire—such as Nitinol—to provide shape-setting capability. In the collapsed state, the first anchor 146 may be received through the opening in the second valve leaflet 22. In the expanded state, the first anchor 146 can have a shape and size that does not fit through the opening in the second valve leaflet 22. Although described in certain contexts herein as comprising pledgets or other structures, the anchors 146, 148 may be formed at least in part of bulky suture knots having a width dimension sufficient to prevent the knot/anchor from being drawn back through the opening in the leaflet. Such knot(s) can be formed from a unitary suture with the suture line 150. The connector anchors 146, 148 may be disposed between the clamps/anchors of the prosthetic device 100 and the respective leaflets prior to removal of the prosthetic device 100.

Figure 14:
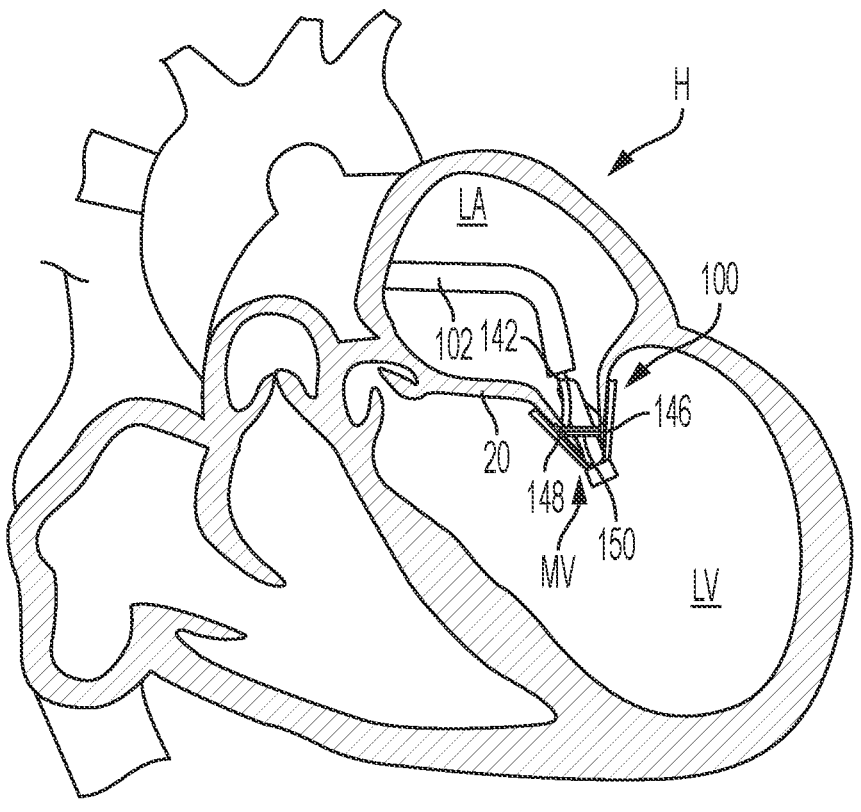

Referring to FIGS. 14 and 15, once the connector 140 is installed onto the second valve leaflet 22, the secondary delivery sheath or secondary means for delivery 142 may be steered such that the distal end 144 is positioned adjacent the atrial side of the first valve leaflet 20 and the suture line 150 extends between the leaflets 20, 22.

Once the distal end 144 is adjacent the atrial side of the first valve leaflet 20, the first valve leaflet 20 may be pierced in the same manner as described regarding the second valve leaflet 22. Once the first valve leaflet 20 has been pierced, the suture line 150 may be extended through the opening formed in the first valve leaflet 20 and the second anchor 148 may be attached to or formed in the suture line 150 adjacent the second valve leaflet 22 to secure the suture line 150 to the first valve leaflet 20. The second anchor 148 can be substantially similar to the first anchor 146 and may be deployed or formed in the same manner as the first anchor 146. In other embodiments, however, the first anchor 146 and the second anchor 148 may be different.

Figure 16:
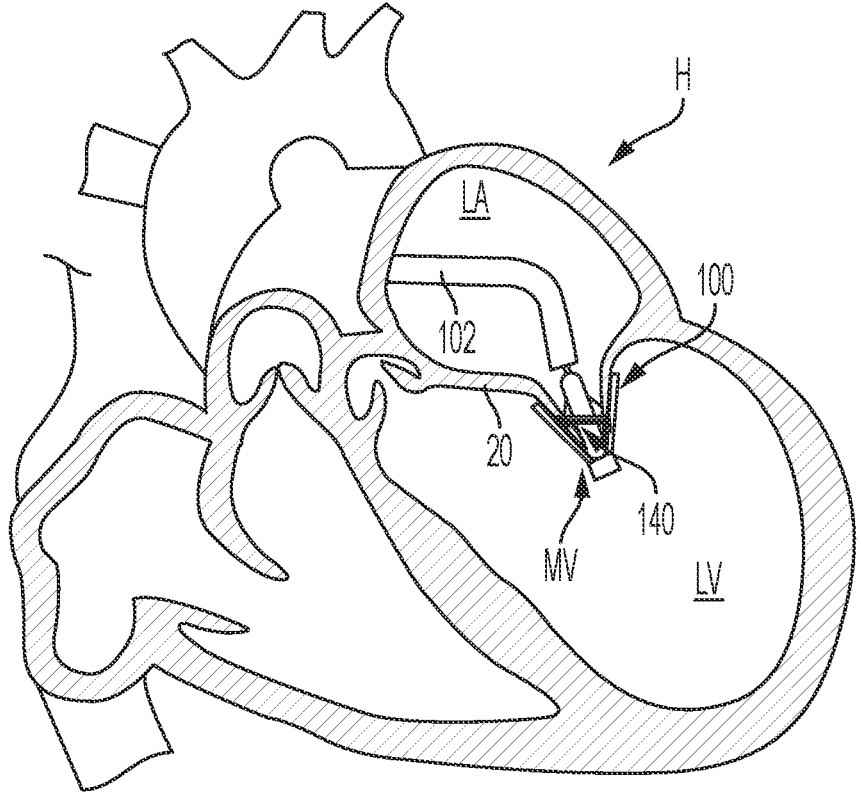

Referring to FIG. 16, with the connector(s) 140 in place, the first anchor 146 and the second anchor 148 can be positioned against the ventricular side of the second valve leaflet 22 and first valve leaflet 20, respectively. The suture line 150 extends from the first anchor 146 to the second anchor 148 through both of the valve leaflets 20, 22. In this way, the connector 140 can hold the valve leaflets 20, 22 together in the area of the connector 140. In some embodiments, the remaining suture line 150 extending from the second anchor 148 up through the secondary delivery sheath or secondary means for delivery 142 can be cut to detach the secondary delivery sheath or secondary means for delivery 142 from the connector 140 and the secondary delivery sheath or secondary means for delivery 142 can be withdrawn.

Figure 17:
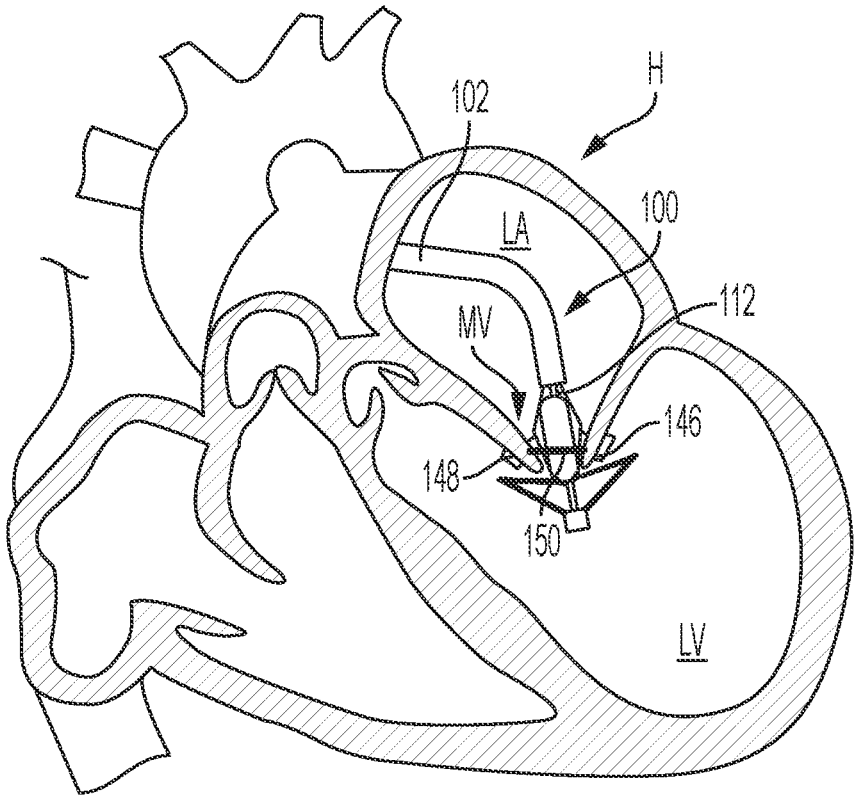
Figure 18:
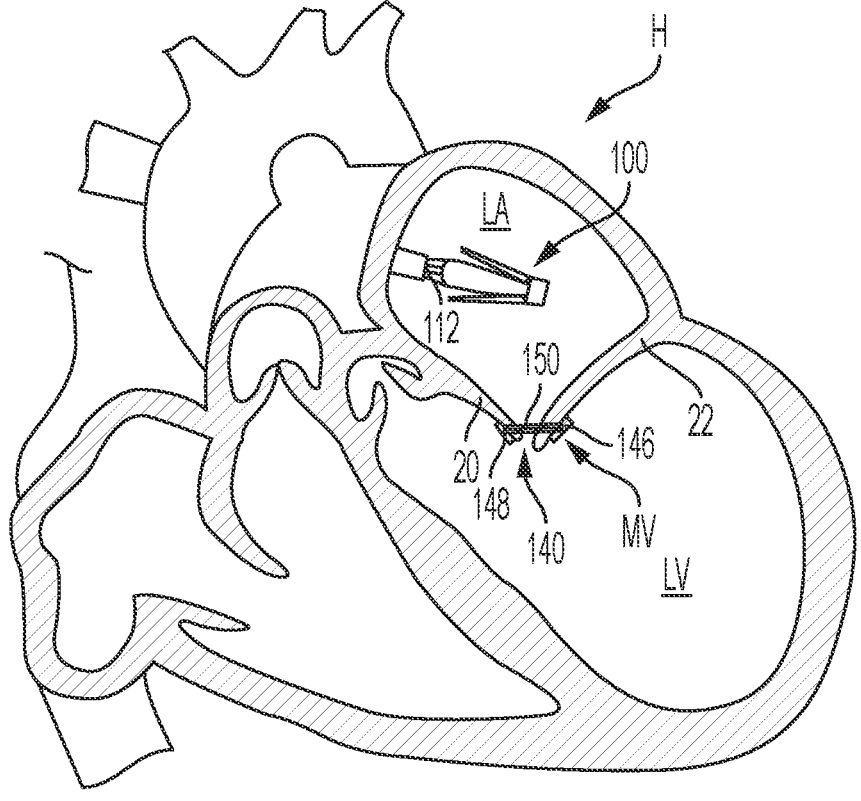

Referring to FIG. 17-18, with the connector 140 in place, the implantable prosthetic device 100 can be kept in place and work in conjunction with the one or more connectors 140, or, as illustrated, can be removed such that the one or more connectors 140 holds the valve leaflets together without the ongoing assistance of the implantable prosthetic device 100.

To remove the implantable prosthetic device 100, the actuation lines 116 can be retracted to open the clasps 130 and release each of the valve leaflet 20, 22. The actuation wire or means for actuating 112 can then be extended to move the implantable prosthetic device 100 into the fully open condition shown in FIG. 7 or another position that allows the prosthetic device 100 to be removed. The implantable prosthetic device 100 and the delivery sheath or means for delivery 102 are then retracted from the left atrium LA through the septum.

Figure 19:
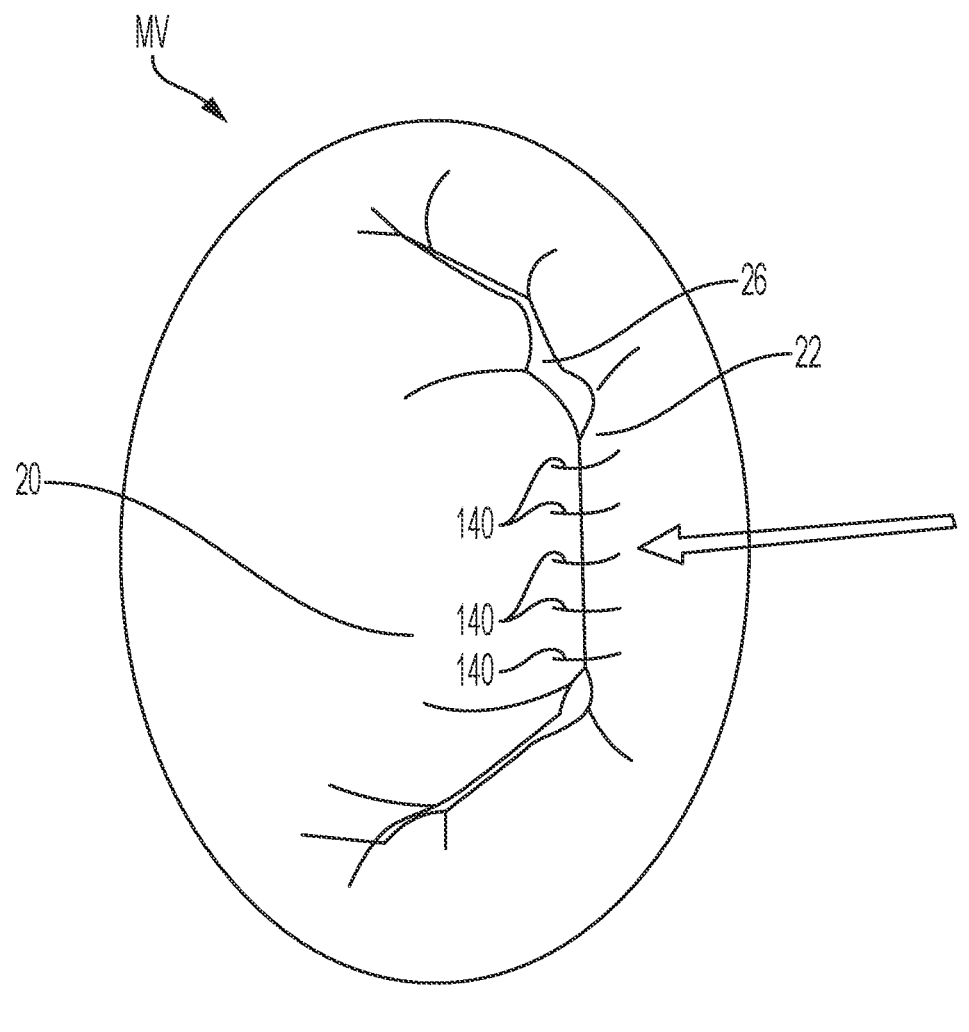
FIG. 19 shows a mitral valve with the leaflets sutured together in multiple locations as viewed from an atrial side of the mitral valve.

Referring to FIG. 19, the atrial side of the mitral valve MV is shown with a plurality of connectors 140 installed. In particular, five separate connectors 140, in the form of anchored sutures, extend from the first valve leaflet 20 to the second valve leaflet 22 to close the gap 26 and prevent regurgitation of blood through the mitral valve MV. In the illustrated embodiment, the five connectors 140 are evenly spaced from each other and parallel. In other embodiments, however, the number of connectors 140 can be greater than five or less than five and the connectors 140 may not be parallel to each other or evenly spaced.

Figure 20:
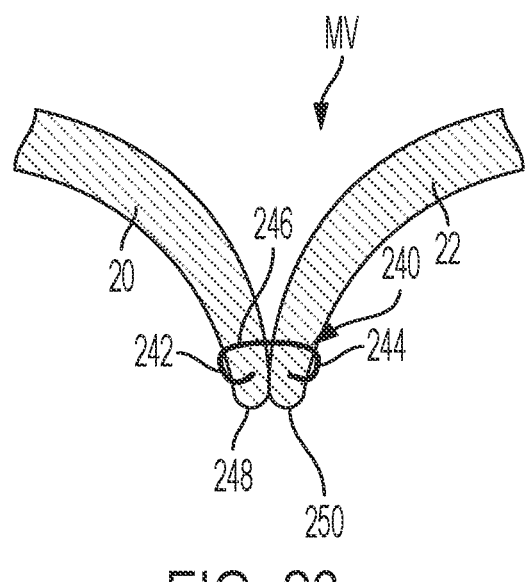
FIG. 20 illustrates a mitral valve with the leaflets attached together by an exemplary embodiment of an attachment device deployed by the prosthetic device.

Referring to FIG. 20, another exemplary embodiment of a connector 240 is shown installed in the first valve leaflet 20 and second valve leaflet 22 of the mitral valve MV. The connector 240 may be configured in a variety of ways. In the illustrated embodiment, the connector 240 is formed as a staple or wire having a first end 242 connected to an opposite a second end 244 by an intermediate connecting portion 246. The connecting portion 246 extends from the ventricular side of the first valve leaflet 20 through both the first valve leaflet 20 and the second valve leaflet 22 to the ventricular side of the second valve leaflet 22. Thus, the connecting portion 246 serves to connect the first valve leaflet 20 and the second valve leaflet 22.

The first end 242 and the second end 244 serve as anchors to attach or anchor the connector 240 to the first valve leaflet 20 and the second valve leaflet 22. As shown in FIG. 16, both the first end 242 and the second end 244 can be curved or curled downward toward the tips 248, 250 of the first valve leaflet 20 and the second valve leaflet 22 (i.e. toward the left ventricle) and inward into the first valve leaflet 20 and the second valve leaflet 22. Thus, the first end 242 and the second end 244 of the connector 240 may pierce into the first valve leaflet 20 and the second valve leaflet 22, respectively, to secure the connector 240 to the leaflets 20, 22. In the illustrated embodiment, the first end 242 and the second end 244 of the connector 240 are imbedded into the first valve leaflet 20 and the second valve leaflet 22, respectively.

The connector 240 may be made of any suitable material or materials. In one exemplary embodiment, the connector 240 is made from, or includes, a shape-memory alloy wire—such as Nitinol—to provide shape-setting capability. In a free state, the illustrated connector 240 has the shape illustrated in FIG. 20. In other embodiments, however, the connector 240 may be shaped differently. Any shape that allows the connector 240 to anchor into and connect the leaflets 20, 22 may be used.

The use of shape-memory alloy materials can allow the connector 240 to be delivered and deployed through, for example, the secondary delivery sheath or secondary means for delivery 142 discussed in relation to the embodiment of FIGS. 13-18. Thus, the connector 240, within the secondary delivery sheath or secondary means for delivery 142, may be in a generally elongated configuration. For example, the open distal end 144 of the secondary delivery sheath or secondary means for delivery 142 may be steered such that the distal end 144 is positioned adjacent the atrial side of the first valve leaflet 20. A piercing device (not shown) may be delivered through the secondary delivery sheath or secondary means for delivery 142 to the distal end 144 and extended or pushed through the first valve leaflet 20 to create an opening in the first valve leaflet 20. Alternatively, the first end 242 of the connector 240 or the distal end 144 may be configured as a piercing device and used to create an opening in the first valve leaflet 20.

Once the first valve leaflet 20 has been pierced, the connector 240 may be delivered through the secondary delivery sheath or secondary means for delivery 142 to the distal end 144 and extended or pushed through the opening in the first valve leaflet 20. Once the first end 242 of the connector 240 exits the distal end 144, the shape-setting capability of the material of the connector 240 cause the first end 242 to revert to its free state. In the illustrated embodiment, the first end 242 curls downward and inward to embed into the ventricular side of the first valve leaflet 20.

Once the connector 240 is installed onto the first valve leaflet 20, the secondary delivery sheath or secondary means for delivery 142 may be steered such that the distal end 144 is positioned adjacent the atrial side of the second valve leaflet 22. The second valve leaflet 22 may be pierced in the same manner as described regarding the first valve leaflet 20.

Once the second valve leaflet 22 has been pierced, the second end 244 of the connector 240 may be delivered extended or pushed through the opening in the second valve leaflet 22. Once the second end 244 of the connector 240 exits the distal end 144, the shape-setting capability of the material of the connector 240 causes the second end 244 to revert to its free state. In the illustrated embodiment, the second end 244 curls downward and inward to embed into the ventricular side of the second valve leaflet 22. Thus, the first end 242 is anchored in the first valve leaflet 20, the second end 244 is anchored in the second valve leaflet 22, and the connecting portion 246 connects the first valve leaflet 20 and the second valve leaflet 22.

In the illustrated embodiment, the connecting portion 246 is slightly curved. In other embodiments, however, the connecting portion 246 can be any suitable shape, such as straight, less curvature, or more curvature.

It will be understood that, similar to the connectors 140 shown in FIG. 9, more than one connector 240 may be used to extend from the first valve leaflet 20 to the second valve leaflet 22 to close the gap 26 and prevent regurgitation of blood through the mitral valve MV. Furthermore, the connector 246 may be implanted while a prosthetic leaflet-holding device, such as or similar to the device 100 described above or other clip or clamp device, holds the leaflets together. That is, any of the connectors described in any of the embodiments in FIGS. 20-26 may be deployed with a prosthetic leaflet-holding device in place to facilitate the placement of the connector(s). For clarity and convenience, suture-holding prosthetic devices are not shown in FIGS. 20-26 allow for greater detail of illustration with respect to the respective connector(s) shown.

Figure 21:
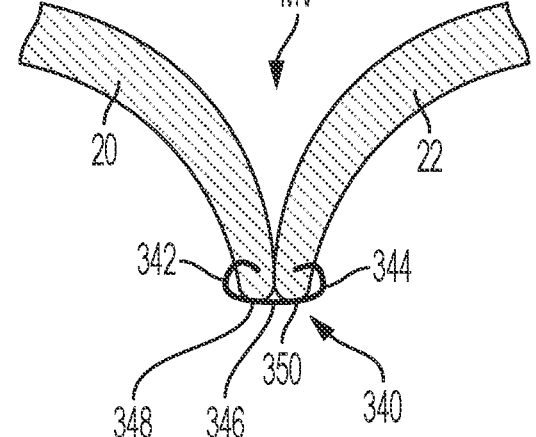
FIG. 21 illustrates a mitral valve with the leaflets attached together by another exemplary embodiment of an attachment device deployed by the prosthetic device.

Referring to FIG. 21, another exemplary embodiment of a connector 340 is shown installed in the first valve leaflet 20 and second valve leaflet 22 of the mitral valve MV. The connector 340 is substantially similar to the connector 240 in that it is formed as a staple or wire having a first end 342 connected to an opposite a second end 344 by a connecting portion 346. The first end 342 and the second end 344 serve as anchors to attach or anchor the connector 340 to the first valve leaflet 20 and the second valve leaflet 22, respectively. As with the connector 240, the connector 340 may be formed from or include a shape-memory alloy wire—such as Nitinol—to provide shape-setting capability.

As shown in FIG. 21, when installed however, the first end 342 and the second end 344 of connector 340 curve or curl upward toward the base of the first valve leaflet 20 and the second valve leaflet 22 (i.e. toward the left atrium) and inward into the first valve leaflet 20 and the second valve leaflet 22. In addition, the connecting portion 346 does not extend through openings in the valve leaflets 20, 22. Instead, the connecting portion 346 extends around the tips 348, 350 of the valve leaflets 20, 22, respectively.

During installation, instead of positioning the distal end 144 of the secondary delivery sheath or secondary means for delivery 142 adjacent the atrial side of the valve leaflets 20, 22 in order to pierce the leaflets 20, 22, the distal end 144 is steered to the ventricular side of the valve leaflets 20, 22. In particular, the secondary delivery sheath or secondary means for delivery 142 may be extended into the left ventricle and steered such that the distal end 144 is adjacent the ventricular side of the first valve leaflet 20. The connector 340 may be delivered through the secondary delivery sheath or secondary means for delivery 142 and out of the distal end 144. Once the first end 342 of the connector 340 exits the distal end 144, the shape-setting capability of the material of the connector 340 cause the first end 342 to revert to its free state. In the illustrated embodiment, the first end 342 curls upward and inward to embed into the ventricular side of the first valve leaflet 20.

Once the connector 340 is installed onto the first valve leaflet 20, the secondary delivery sheath or secondary means for delivery 142 may be steered such that the distal end 144 is positioned adjacent the ventricular side of the second valve leaflet 22 and the second end 344 of the connector 340 may be extended or pushed out of the distal end 144. Once the second end 344 exits the distal end 144, the shape-setting capability of the material of the connector 340 cause the second end 344 to revert to its free state. In the illustrated embodiment, the second end 344 curls upward and inward to embed into the ventricular side of the second valve leaflet 22. Thus, the first end 342 is anchored in the first valve leaflet 20, the second end 344 is anchored in the second valve leaflet 22, and the connecting portion 246 extends around the valve leaflet tips 348, 350 to connect the first valve leaflet 20 and the second valve leaflet 22.

In the illustrated embodiment, the connecting portion 346 is slightly curved. In other embodiments, however, the connecting portion 346 can be any suitable shape, such as straight, less curvature, or more curvature.

Figure 22:
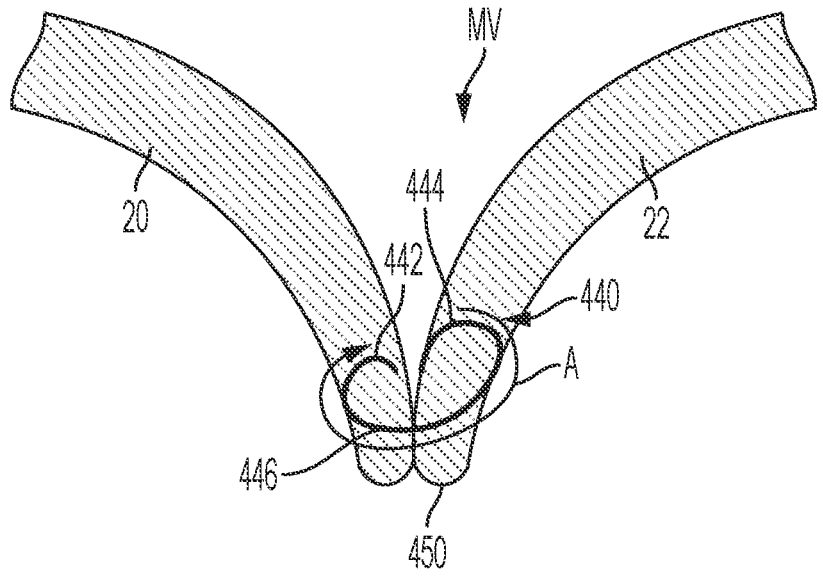
FIG. 22 illustrates a mitral valve with the leaflets attached together by another exemplary embodiment of an attachment device deployed by the prosthetic device.

Referring to FIG. 22, another exemplary embodiment of a connector 440 is shown installed in the first valve leaflet 20 and second valve leaflet 22 of the mitral valve MV. The connector 440 is similar to the connector 340 in that it is formed as a staple or wire having a first end 442 connected to an opposite a second end 444 by a connecting portion 446. The first end 442 and the second end 344 serve as anchors to attach or anchor the connector 440 to the first valve leaflet 20 and the second valve leaflet 22, respectively. As with the connector 240, the connector 440 may be formed from or include a shape-memory alloy wire—such as Nitinol—to provide shape-setting capability. In the illustrated embodiment, the connector 440 has a continuous curled shape.

During installation, the open distal end 144 of the secondary delivery sheath or secondary means for delivery 142 may be steered such that the distal end 144 is positioned adjacent the atrial side of the second valve leaflet 22. The first end 342 of the connector 240 may be configured as a piercing device and used to create an opening in the second valve leaflet 22.

The connector 440 may be delivered through the secondary delivery sheath or secondary means for delivery 142 to the distal end 144 and extended or pushed into the first valve leaflet 20. Once the first end 442 of the connector 440 exits the distal end 144, the shape-setting capability of the material of the connector 240 cause the portion of the connector 440 deployed from the secondary delivery sheath or secondary means for delivery 142 to revert to its free state. In the illustrated embodiment, the first end 442 of the connector 440 follows the curved path shown by arrow A as the connector 440 deployed from the secondary delivery sheath or secondary means for delivery 142. In particular, the first end 442 extends through the second valve leaflet 22 in a downward curved path before exiting the atrial side of the second valve leaflet 22 at a location closer to the tip 450 of the second valve leaflet 22 than the location where the first end 442 initially entered the second valve leaflet 22. After exiting the atrial side of the second valve leaflet 22, the first end enters the atrial side of the first valve leaflet 20 and extends in an upward curved path until the second end 444 exits the distal end 144 of the secondary delivery sheath or secondary means for delivery 142 (i.e., the connector 440 is fully installed).

In the illustrated embodiment, the connector 440 is not exposed on the ventricular sides of the first and second valve leaflets 20, 22. In other embodiments, however, as the first end 442 tunneled the curved path through the first and second valve leaflets 20, 22, the first end 442 may exit and reenter the ventricular sides of the first and second valve leaflets 20, 22. Thus, a portion of the embedded connector 440 may be exposed on the ventricular sides of the first and second valve leaflets 20, 22

Referring to FIGS. 23-26, another exemplary embodiment of a connector 540 is shown being installed in the first valve leaflet 20 and second valve leaflet 22 of the mitral valve MV. The connector 540 is similar to the connector 140 of FIGS. 13-18 in that the connector 540 includes a first anchor 546 positioned on the ventricular side of the second valve leaflet 22 for anchoring a suture line to the second valve leaflet 22 and a second anchor 548 positioned on the ventricular side of the first valve leaflet 20 for anchoring a suture line to the first valve leaflet 20.

However, while the connector 140 has a suture line 150 that extends between the first anchor 146 and the second anchor 148, the connector 540 has a first suture line 550 attached to the first anchor 546 and a separate, second suture line 552 attached to the second anchor 548. The connector 540 also includes a suture-locking device 554 configured to capture first suture line 550 and second suture line 552 and lock them in position relative to the suture-locking device 554.

The connector 540 can be delivered and deployed through, for example, one or more delivery sheathes or means for delivery in a similar manner as discussed in relation to the embodiment of FIGS. 13-18. The first anchor 546 and first suture line 550 may be deployed via the same delivery sheath or means for delivery as the second anchor 548 and second suture line 552 or may be deployed via a different delivery sheath or secondary means for delivery.

Figure 23:
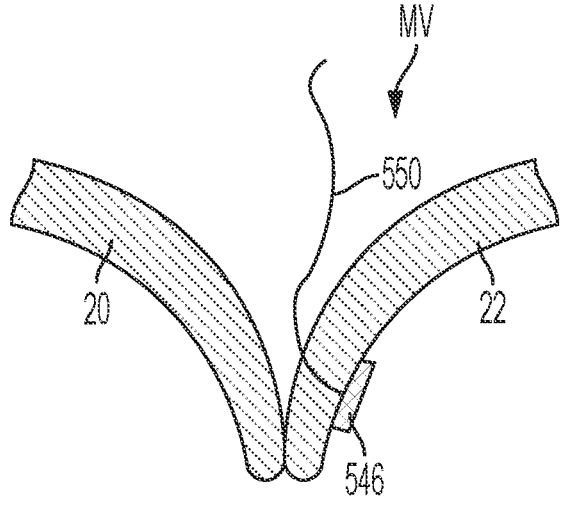
FIGS. 23-26 illustrates a mitral valve with an exemplary embodiment of a suture attaching the valve leaflets together.
Figure 24:
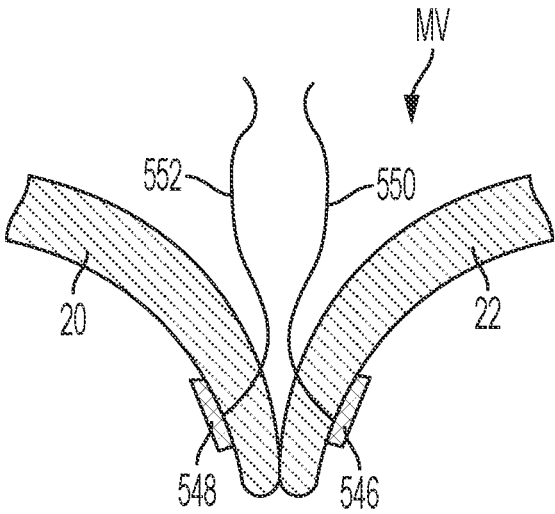

As shown in FIGS. 23-24, the second valve leaflet 22 may be pierced and the first anchor 546 may be positioned on the ventricular side of the second valve leaflet 22 with the first suture line 550 extending through the second valve leaflet 22. Similarly, the first valve leaflet 20 may be pierced and the second anchor 548 may be positioned on the ventricular side of the first valve leaflet 20 with the second suture line 552 extending through the first valve leaflet 20.

The suture-locking device 554 can be deployed via the delivery sheath or means for delivery 102. The suture-locking device 554 may be mounted onto the first and second suture lines 550, 552 such that the first and second suture lines 550, 552 extend through the suture-locking device 554. The suture-locking device 554 may be mounted onto the first and second suture lines 550, 552 prior to the suture-locking device 554 being deployed via the delivery sheath or means for delivery 102 or in the left atrium, after the suture-locking device 554 exits the delivery sheath or means for delivery 102.

The suture-locking device 554 may be configured in a variety of ways. Any device that can facilitate drawing the first and second valve leaflets 20, 22 together and locking the first and second suture lines 550, 552 in place in order to hold the first and second valve leaflets 20, 22 together may be used. In the illustrated embodiment, the suture-locking device includes a wedge-type device 556 and a locking nut/clip 558.

Figure 25:
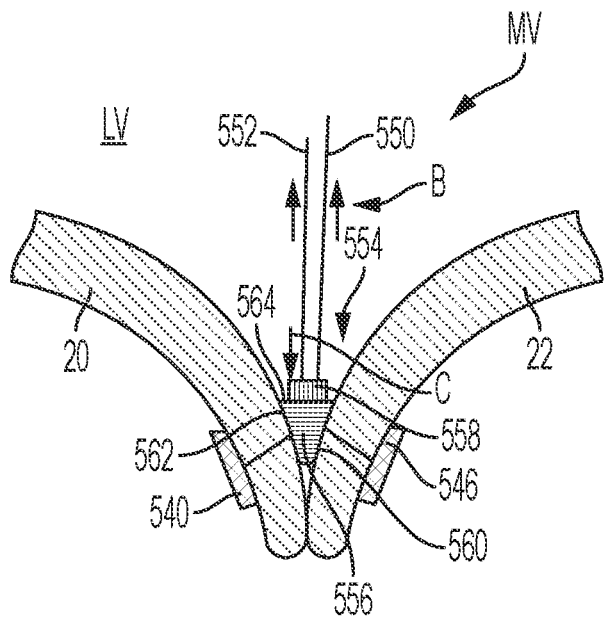
Figure 26:
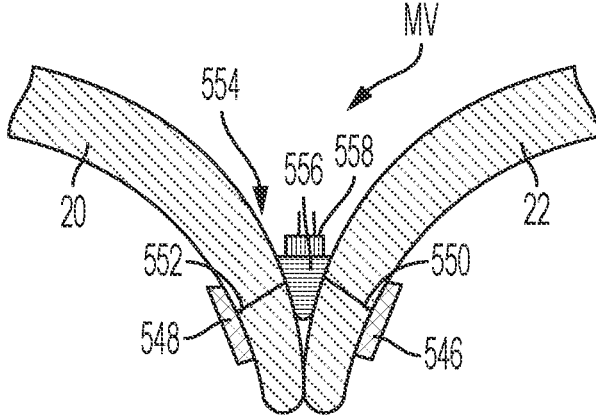

Referring to FIG. 25, the wedge 556 includes a first angled engagement surface 560 having an channel (not shown) that receives the first suture line 550 and a second angled engagement surface 562, opposite the first angled engagement surface 560, having a second channel (not shown) that receives the second suture line 552. The first angled engagement surface 560 and the second angled engagement surface 562 form the tapering wedge shape of the wedge 556 and are connected via a base surface 564. The first suture line 550 and the second suture line 552 exit the wedge 556 via a locking aperture (not shown) in the base surface 564.

The locking nut 558 is configured to, at least partially, be received in the locking aperture. The locking nut 558 is annular and includes an internal, longitudinal passage (not shown) through which the first suture line 550 and the second suture line 552 extend. The locking nut 558 can be configured to attach to the wedge 556 in a manner which locks the first suture line 550 and the second suture line 552 in place relative to the wedge 556. In an exemplary embodiment, the locking nut 558 includes a male threaded portion (not shown) configured to threadably engage a corresponding female threaded portion (not shown) in the locking aperture of the wedge 556. In some embodiments, the locking nut 558 comprises a clip or other form Referring to FIG. 25, when the suture-locking device is positioned such that the first suture line 550 and the second suture line 552 are received through the wedge 556, the first suture line 550 and the second suture line 552 can be pulled in the direction of the left ventricle LV as shown by arrows B in FIG. 25 and the wedge 556 can be pushed in the opposite direction as shown by arrow C. As a result, the first valve leaflet 20 and the second valve leaflet 22 are drawn together such that the wedge 556 is sandwiched between the first valve leaflet 20, which engages the second angled engagement surface 562, and the second valve leaflet 22, which engages the second angled engagement surface 562.

To lock the first valve leaflet 20 and the second valve leaflet 22 together, the locking nut 558 can be attached to the wedge 556 to capture the first suture line 550 and the second suture line 552 between the locking nut 558 and the wedge 556. For example, the locking nut 558 can be threaded into the lacking aperture until the first suture line 550 and the second suture line 552 are sandwiched between the locking nut 558 and an interior surface of the wedge 556.

Once the first suture line 550 and the second suture line 552 are captured between the locking nut 558 and the wedge 556, the first suture line 550 and the second suture line 552 can be cut external to the locking nut 558.

While various inventive aspects, concepts and features of the disclosures may be described and illustrated herein as embodied in combination in the exemplary embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein.

Additionally, even though some features, concepts, or aspects of the disclosures may be described herein as being a preferred arrangement or method, such description is not intended to suggest that such feature is required or necessary unless expressly so stated. Still further, exemplary or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of exemplary methods or processes are not limited to inclusion of all steps as being required in all cases, nor is the order that the steps are presented to be construed as required or necessary unless expressly so stated. The words used in the claims have their full ordinary meanings and are not limited in any way by the description of the embodiments in the specification.

What is claimed is:

1. A heart valve repair system comprising:
    an implantable device configured to attach to at least two leaflets of a native heart valve of a patient and hold the at least two leaflets in a relatively fixed position; and a connector that is separate from the implantable device, the connector including first and second tissue anchors and being configured to be attached to the at least two leaflets of the native heart valve of the patient when the at least two leaflets are held by the implantable device in the relatively fixed position;

wherein the connector includes a wedge and a locking nut;

the connector having angled engagement surfaces that are configured to engage the at least two leaflets of the native valve and having a base surface with a locking aperture;

a first suture attached to the first anchor;

a second suture attached to the second anchor;

wherein the first suture and the second suture are received by the angled engagement surfaces, exit the wedge through the base surface and extend through an internal passage of the locking nut;

wherein the locking nut is configured to be at least partially received in the locking aperture;

wherein the locking nut is configured to capture the first suture and the second suture between the locking nut and the wedge; and the implantable device being configured to be detached from the at least two leaflets and removed from the patient with the connector remaining attached to the at least two leaflets.

2. The heart valve repair system of claim 1, wherein the implantable device is configured both to allow the implantable device to remain attached to the native heart valve after the connector is attached to the native heart valve and to allow the implantable device to be removed from the native heart valve after the connector is attached to the native heart valve.

3. The heart valve repair system of claim 2, wherein the implantable device includes a spacer element.

4. The heart valve repair system of claim 1, wherein the implantable device includes a plurality of paddles that each comprise an inner paddle portion and an outer paddle portion.

5. The heart valve repair system of claim 1, wherein the implantable device and the connector are configured to close a gap in the native heart valve of the patient when the valve repair system is attached to the native heart valve.

6. The heart valve repair system of claim 1, wherein the first anchor comprises a pledget.

7. The heart valve repair system of claim 1, wherein the implantable device includes a first anchor configured to embed into a first valve leaflet and a second anchor configured to embed into a second valve leaflet.

8. The heart valve repair system of claim 1, wherein the locking nut is configured to be threaded into the locking aperture until the first suture line and the second suture line are sandwiched between the locking nut and an interior surface of the wedge.

9. The heart valve repair system of claim 1, wherein the locking nut is sized such that the locking nut and the base surface form a step.

10. The heart valve repair system of claim 1, wherein the locking nut is sized such that the locking nut is spaced apart from the at least two leaflets of the native heart valve.

11. A valve repair system comprising:

an implantable device comprising:

first and second paddles that are movable between an open position and a closed position;

first and second tissue-gripping elements associated with the first and second paddles, respectively, each of the first and second tissue-gripping elements being configured to attach to a respective leaflet of a native heart valve of a patient;

a connector configured to be implanted in first and second leaflets of the native heart valve of the patient when the implantable device is gripped to the first and second leaflets and to allow for the implantable device to be removed when the connector is implanted in the first and second leaflets, the connector comprising:

a first anchor configured to engage a first valve leaflet of the native heart valve of the patient;

a second anchor configured to engage a second valve leaflet of the native heart valve of the patient;

a first suture attached to the first anchor;

a second suture attached to the second anchor;

wherein the first suture and the second suture extend between the first anchor and the second anchor;

a wedge having angled engagement surfaces that are configured to engage the first valve leaflet and the second valve leaflet between the first anchor and the second anchor and having a base surface with a locking aperture;

a locking nut at least partially received in the locking aperture;

wherein the first suture and the second suture are received by the angled engagement surfaces, exit the wedge through the base surface, and extend through an internal passage of the locking nut; and wherein the locking nut is configured to capture the first suture and the second suture between the locking nut and the wedge.

12. The valve repair system of claim 11, wherein the implantable device is configured both to allow the implantable device to remain attached to the native heart valve after the connector is attached to the native heart valve and to allow the implantable device to be removed from the native heart valve after the connector is attached to the native heart valve.

13. The valve repair system of claim 11, wherein each of the first and second paddles comprise an inner paddle portion and an outer paddle portion.

14. The valve repair system of claim 11, wherein the connector is configured to keep a gap in the native heart valve of the patient closed after the implantable device is removed.

15. The valve repair system of claim 11, wherein the first anchor comprises a pledget.

16. The valve repair system of claim 11, wherein the first anchor is configured to embed into the first valve leaflet and the second anchor is configured to embed into the second valve leaflet.

17. The valve repair system of claim 11, wherein the locking nut is configured to be threaded into the lacking aperture until the first suture line and the second suture line are sandwiched between the locking nut and an interior surface of the wedge.

18. The valve repair system of claim 11, wherein the locking nut is sized such that the locking nut and the base surface form a step.

19. The valve repair system of claim 11, wherein the locking nut is sized such that the locking nut is spaced apart from the at least two leaflets of the native heart valve.

20. A heart valve repair system comprising:

an implantable device configured to attach to at least two leaflets of a native heart valve of a patient and hold the at least two leaflets in a relatively fixed position; and a connector that is separate from the implantable device, the connector including first and second tissue anchors and being configured to be attached to the at least two leaflets of the native heart valve of the patient when the at least two leaflets are held by the implantable device in the relatively fixed position;

wherein the connector includes a wedge and a lock;

the connector having angled engagement surfaces that are configured to engage the at least two leaflets of the native valve and having a base surface;

a first suture attached to the first anchor;

a second suture attached to the second anchor;

wherein the first suture and the second suture are received by the angled engagement surfaces, exit the wedge through the base surface and extend through an internal passage of the lock; and the implantable device being configured to be detached from the at least two leaflets and removed from the patient with the connector remaining attached to the at least two leaflets.

\*  \*  \*  \*  \*